US011110373B2

(12) United States Patent
Cirou et al.

(10) Patent No.: US 11,110,373 B2
(45) Date of Patent: *Sep. 7, 2021

(54) INSTALLATION FOR TREATING BIOLOGICAL LIQUID

(71) Applicant: EMD Millipore Corporation, Burlington, MA (US)

(72) Inventors: Sebastien Cirou, Hochstati (FR); Christine Abouayad El Idrissi, Eschau (FR)

(73) Assignee: EMD Millipore Corporation, Burlington, MA (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/349,791

(22) PCT Filed: Mar. 6, 2018

(86) PCT No.: PCT/US2018/021148
§ 371 (c)(1),
(2) Date: May 14, 2019

(87) PCT Pub. No.: WO2018/182931
PCT Pub. Date: Oct. 4, 2018

(65) Prior Publication Data
US 2019/0358561 A1 Nov. 28, 2019

(30) Foreign Application Priority Data

Mar. 29, 2017 (EP) ..................................... 17305363

(51) Int. Cl.
*B01D 15/04* (2006.01)
*B01D 15/00* (2006.01)
(Continued)

(52) U.S. Cl.
CPC ............. *B01D 15/14* (2013.01); *B01D 15/00* (2013.01); *B01D 15/08* (2013.01);
(Continued)

(58) Field of Classification Search
CPC ........ B01D 15/00; B01D 15/08; B01D 15/14; B01D 15/1871; C12M 23/44;
(Continued)

(56) References Cited

U.S. PATENT DOCUMENTS 5,468,847 A * 11/1995 Heilmann ............... B01D 15/08
210/500.23
7,846,335 B2 12/2010 Bisschops et al.
(Continued)

FOREIGN PATENT DOCUMENTS

| CN | 101597320 A | 12/2009 |
|---|---|---|
| CN | 101758843 A | 6/2010 |

(Continued)

OTHER PUBLICATIONS

International Search Report and Written Opinion received for PCT Application No. PCT/US2018/021153, dated Jun. 28, 2018, 9 pages.

(Continued)

*Primary Examiner* — John Kim
(74) *Attorney, Agent, or Firm* — EMD Millipore Corporation

(57) ABSTRACT

The invention concerns an installation for treating biological liquid by chromatography, extending in a longitudinal direction and comprising a supply valve (20*b*), a supply pump (30) downstream of the valve, instrument members downstream of the pump among which are at least one distribution valve (81*a-c*, 82*a-c*, 83*a-c*) and at least one device (78*a-c*, 85*a-c*, 86*a-c*) for measuring a physico-chemical parameter of the liquid, at least one chromatography column (99*a-c*)

(Continued)

downstream of the instrument members and of the pipes connecting the valve, the pump, the instrument members and the column, instrument members being associated with the chromatography column and each mounted on at least one dedicated control and actuation platform (80a-c), which extends in a vertical direction relative to the generally longitudinal direction of extension of said installation, and which are disposed substantially above each other on said dedicated control and actuation platform.

16 Claims, 10 Drawing Sheets

(51) Int. Cl.
    *B01D 15/08*   (2006.01)
    *G01N 30/88*   (2006.01)
    *C12M 1/00*    (2006.01)
    *C12M 3/00*    (2006.01)
    *B01D 15/14*   (2006.01)
    *B01D 15/18*   (2006.01)
    *C12M 1/12*    (2006.01)

(52) U.S. Cl.
    CPC ......... *B01D 15/1871* (2013.01); *C12M 23/44* (2013.01); *C12M 47/12* (2013.01); *G01N 30/88* (2013.01); *C12M 1/12* (2013.01); *G01N 2030/8804* (2013.01)

(58) Field of Classification Search
    CPC ......... C12M 47/12; C12M 1/12; G01N 30/88; G01N 2030/8804
    See application file for complete search history.

(56) References Cited

U.S. PATENT DOCUMENTS

| | | | |
|---|---|---|---|
| 8,133,451 B2* | 3/2012 | Yuan | B01L 3/502715 422/404 |
| 8,182,696 B2 | 5/2012 | Theoleyre et al. | |
| 8,465,649 B2 | 6/2013 | Theoleyre et al. | |
| 9,012,212 B2 | 4/2015 | Bisschops et al. | |
| 9,657,056 B2 | 5/2017 | Konstantinov et al. | |
| 2006/0049209 A1* | 3/2006 | Baker | A61M 5/14216 222/252 |
| 2006/0118472 A1 | 6/2006 | Schick et al. | |
| 2007/0131615 A1 | 6/2007 | Moran et al. | |
| 2009/0049891 A1* | 2/2009 | Shaimi | G01N 30/466 73/23.36 |
| 2009/0294349 A1 | 12/2009 | Beulay et al. | |
| 2010/0144028 A1 | 6/2010 | Bisschops et al. | |
| 2011/0120951 A1* | 5/2011 | Hampton | G01N 30/56 210/657 |
| 2012/0031510 A1* | 2/2012 | Weissenbach | B62B 5/00 137/343 |
| 2013/0280788 A1 | 10/2013 | Skudas | |
| 2015/0183821 A1 | 7/2015 | Konstantinov et al. | |
| 2015/0190809 A1 | 7/2015 | Tuccelli et al. | |
| 2015/0232505 A1 | 8/2015 | Konstantinov et al. | |
| 2018/0021791 A1 | 1/2018 | Spiegel et al. | |
| 2018/0252326 A1 | 9/2018 | Gagne et al. | |
| 2019/0374874 A1 | 12/2019 | Cirou et al. | |

FOREIGN PATENT DOCUMENTS

| | | |
|---|---|---|
| CN | 102372015 A | 3/2012 |
| CN | 202471668 U | 10/2012 |
| CN | 102933286 A | 2/2013 |
| CN | 102939145 A | 2/2013 |
| CN | 102946960 A | 2/2013 |
| EP | 1994972 A1 | 11/2008 |
| EP | 2656892 A1 | 10/2013 |
| EP | 2 675 540 B1 | 3/2018 |
| FR | 2931838 A1 | 12/2009 |
| FR | 2940145 A1 | 6/2010 |
| FR | 2961711 A1 | 12/2011 |
| FR | 2963573 A1 | 2/2012 |
| JP | 2012-55306 A | 3/2012 |
| JP | 2015-520667 A | 7/2015 |
| WO | 2007/043874 A1 | 4/2007 |
| WO | 2007/067882 A2 | 6/2007 |
| WO | 2007/144476 A1 | 12/2007 |
| WO | 2007/144522 A2 | 12/2007 |
| WO | 2008/153472 A1 | 12/2008 |
| WO | 2010/151214 A1 | 12/2010 |
| WO | 2012/074481 A1 | 6/2012 |
| WO | 2015/094095 A1 | 6/2015 |
| WO | 2015/144481 A1 | 10/2015 |
| WO | 2018/182931 A1 | 10/2018 |
| WO | 2018/182932 A9 | 12/2018 |

OTHER PUBLICATIONS

International Search Report and Written Opinion received for PCT Application No. PCT/US2018/021148, dated Jun. 19, 2018, 8 pages.

"International Preliminary Report on Patentability received for PCT Application No. PCT/US2018/021148, dated Oct. 10, 2019", 7 pages.

"International Preliminary Report on Patentability received for PCT Application No. PCT/US2018/021153, dated Oct. 10, 2019", 8 pages.

* cited by examiner

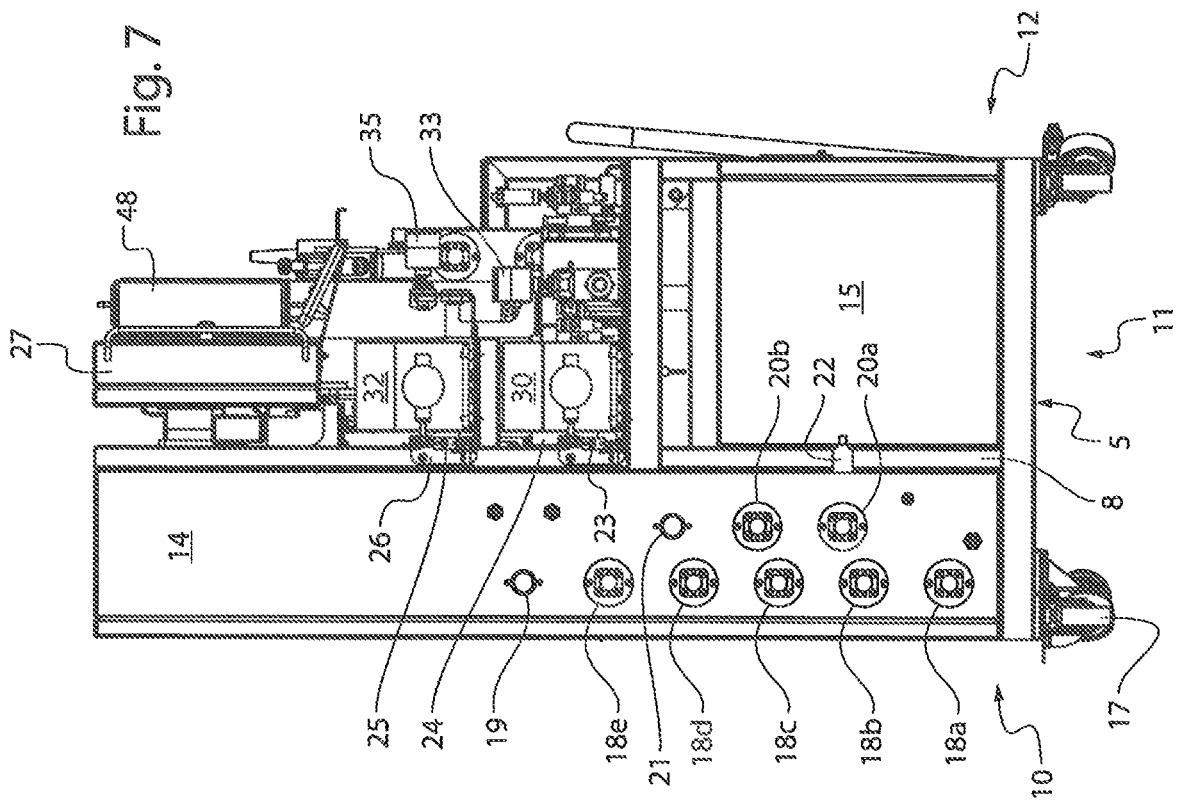
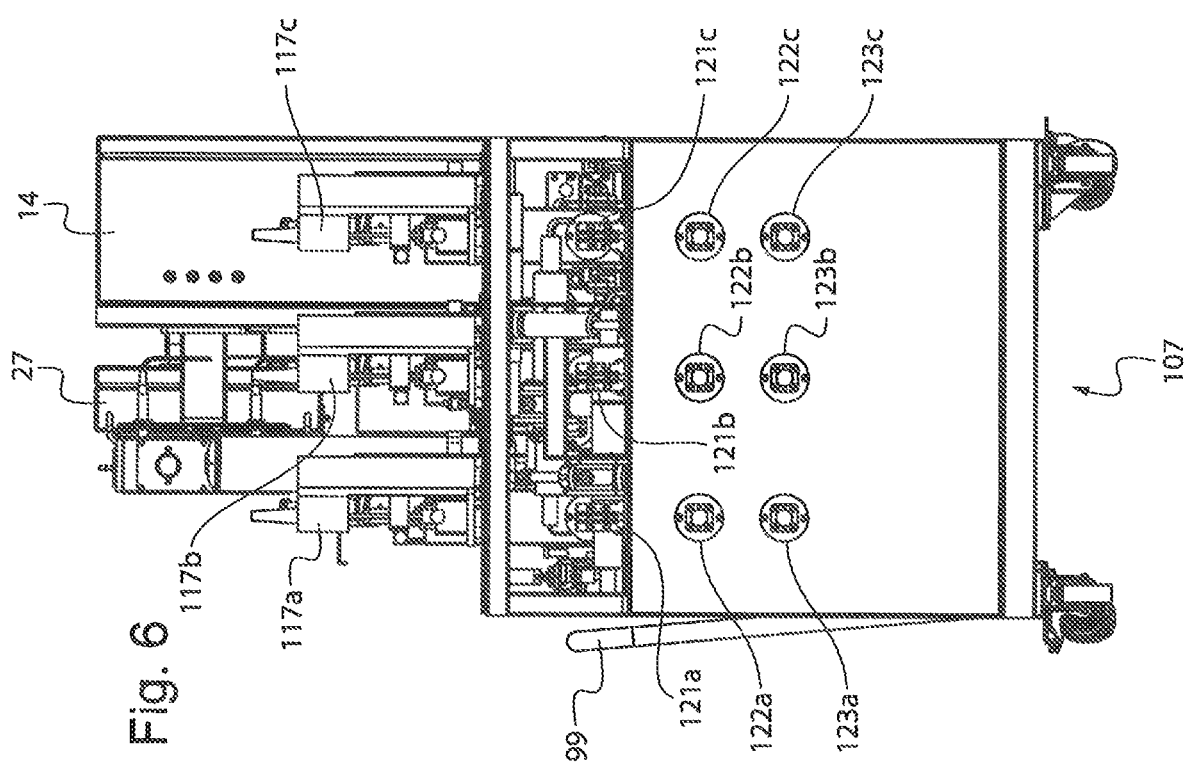

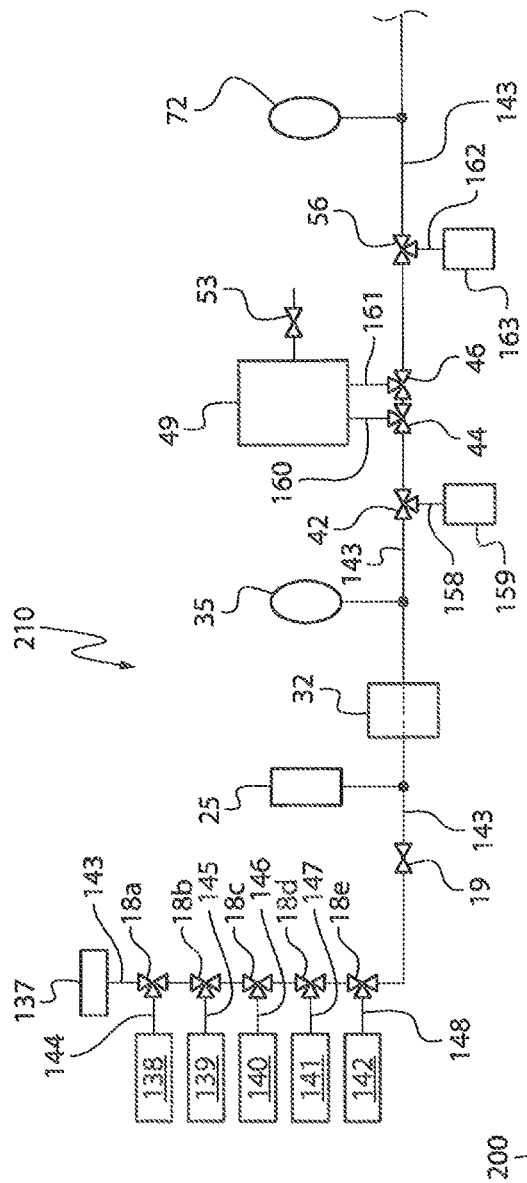
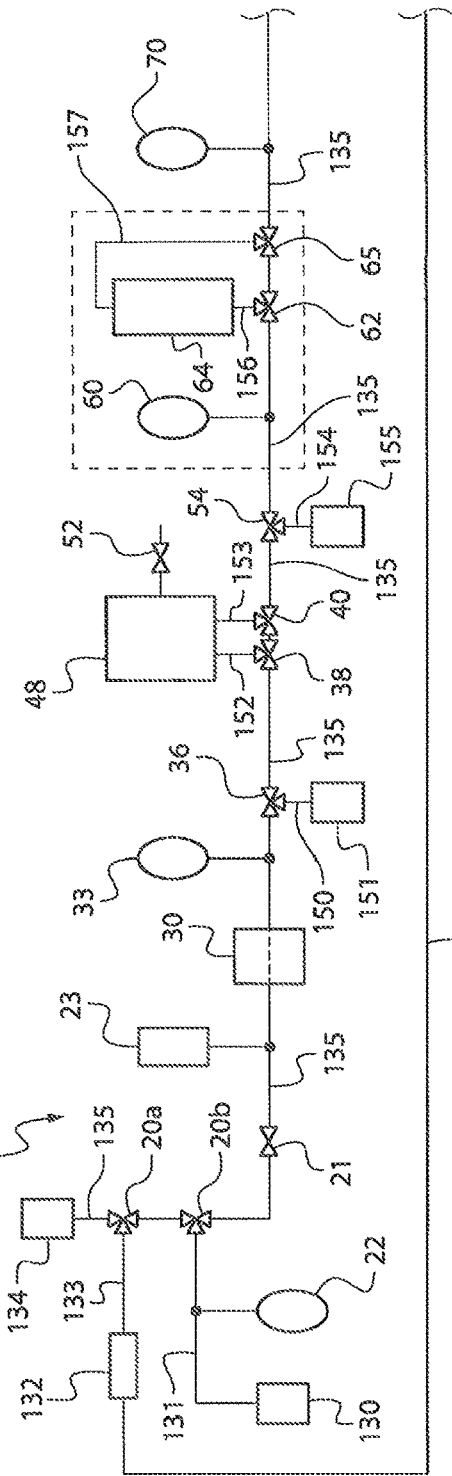
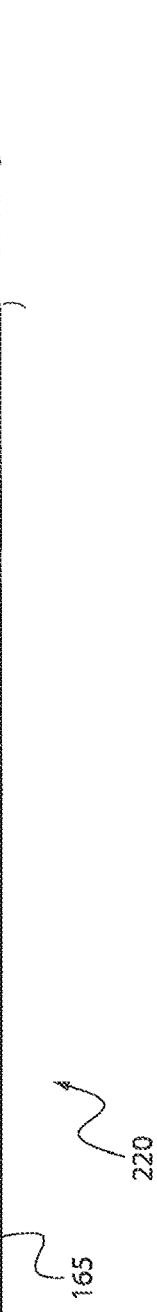
Fig. 12

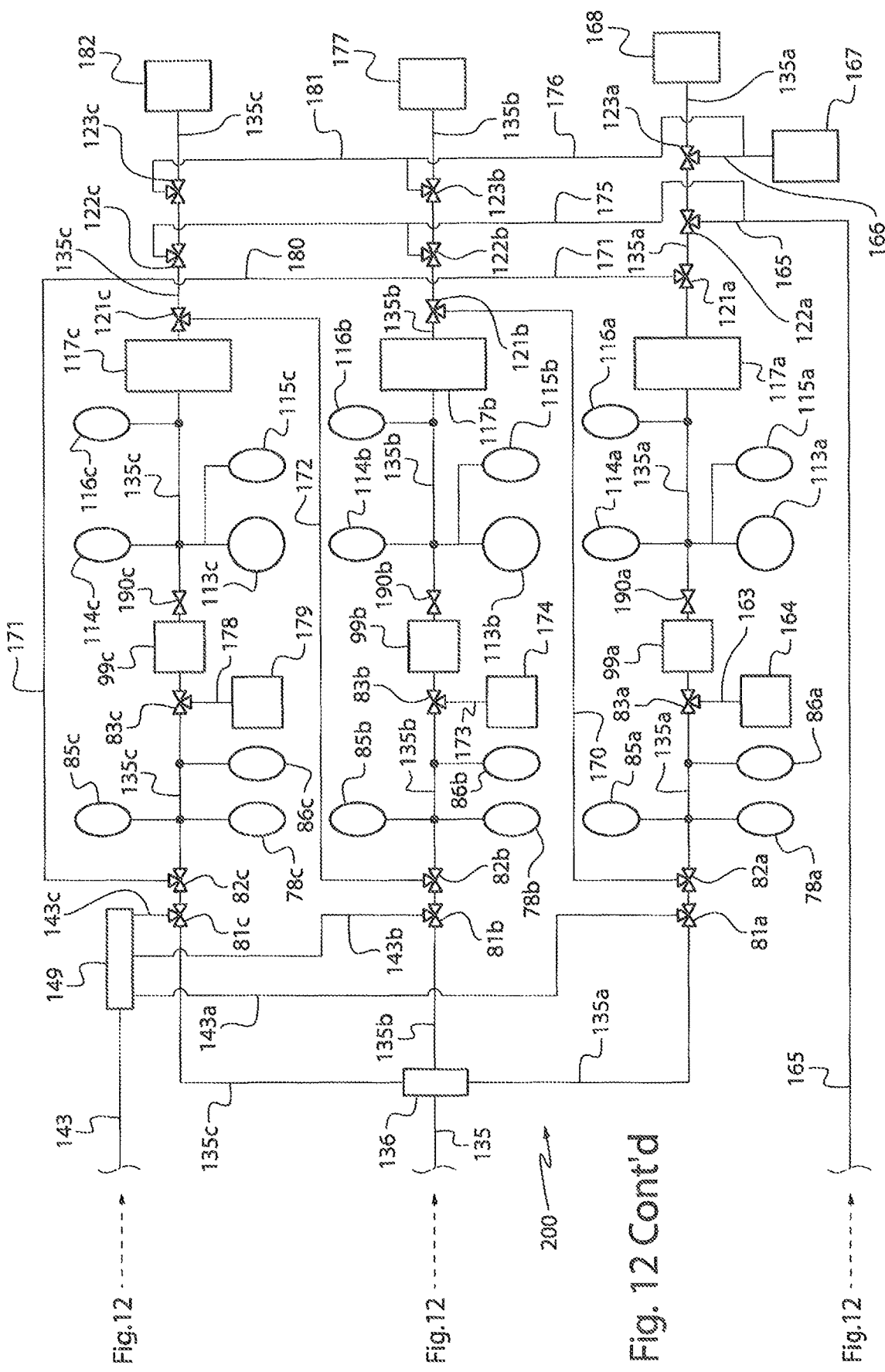

INSTALLATION FOR TREATING BIOLOGICAL LIQUID

CROSS-REFERENCE TO RELATED APPLICATION

The present application is a US National Stage application of International Application No. PCT/US2018/021148, filed Mar. 6, 2018, which claims the benefit of priority of EP Patent Application No. 17305363.8, filed Mar. 29, 2017, each of which is incorporated by reference herein in its entirety.

FIELD OF THE INVENTION

The invention relates to installations for treating biological liquid, in particular, but not exclusively, for purifying a biopharmaceutical liquid in order to obtain a product such as monoclonal antibodies, vaccines or recombinant proteins.

TECHNOLOGICAL BACKGROUND

It is known that biopharmaceutical liquids are in general obtained by cultures in a bioreactor and that they must then be purified to achieve the required characteristics of purity, concentration, absence of viruses, etc.

The purification is generally carried out by means of a succession of treatments such as clarification to eliminate the residues from the bioreactor culture and viral retention treatment sometimes followed by diafiltration treatment and concentration by tangential flow filtration (TFF). Other operations exist concerning purification, such as chromatography (XMO).

The purification treatments are essentially carried out by filtering operations in a circuit leading to a container for collecting the treated liquid. A number of types of container containing liquids can be connected to the inlet of the circuit, such as the source container that contains the product to be treated, but also the containers containing a cleaning liquid such as sodium hydroxide (NaOH), a rinsing liquid such as pure water or a buffer liquid such as a saline solution.

In addition to the container for collecting the treated liquid, various other containers for collecting cleaning, rinsing or buffer liquid, or for collecting residues, can be connected to the outlet of the circuit.

In a production context the liquid treatments can be carried out sequentially, the collecting container for the first treatment potentially becoming the source container for the next treatment, and so on until the last treatment is carried out.

These treatments are conventionally carried out in dedicated installations comprising stainless steel pipes and other parts such as tanks or housings for filters, which necessitate operations before and after the actual treatment, which are relatively onerous, in particular operations of cleaning after use.

Within the last few years, these treatments have alternatively been carried out in installations in which the components in contact with the liquid are single-use components. From document EP 2 585 187 such an installation is known for treatment by chromatography.

This installation comprises a device formed from a base, a press with two shells mounted on a front face of that base, a bag clamped between that press and a support plate fastened on one side of the base. The device has the form of a cart mounted on four castors. The device is also provided, at the bottom, with a closed bay intended to receive one or more tanks if necessary. A control panel is arranged at the top of the front face of the device.

On the front of the shells there are formed shaping channels which are recessed and which face each other to form pipes in the bag and, on the back of the shells are installed instruments among which are pressure sensors and pinch valves which are configured to pinch the pipes so as to prevent or allow the passage of liquid therein. The bag is provided with a plurality of connectors for liquid and a network for conveying liquid between those connectors including the aforementioned pipes. The support plate comprises two fastening heads on which a platform is adapted to be fastened so as to dispose thereon instruments for the treatment of the biological liquid. These instruments may for example be sensors measuring pH or conductivity.

This installation further comprises other devices, of the cart type, on which are disposed pumps, various containers containing for example rinsing, cleaning and/or buffer liquids, and/or an elution product or which are provided to receive a collection, a fraction or waste; other measuring instruments such as a product presence sensor, a debubbler (also called a bubble trap), pressure, pH and/or conductivity sensors; one or more filter components and a chromatography column; all these components being configured to be connected to the circuit of the bag.

From document EP 2 130 903 an installation is also known which comprises a first cart and a second cart which may be either apart or nested with one in the other.

Each cart is of parallelepiped general shape and is mounted on wheels in order to enable its easy movement within a production zone.

The first cart is open on one side and towards the ground, and its interior is hollowed to enable the nesting of the second cart. On the upper part of the first cart is a support platform adapted to receive re-usable components of the circuit and means for supporting the disposable components. Among the re-usable components carried by the platform is in particular a flow pump, a first pressure sensor and a control panel for controlling the pump. The platform is positioned at a sufficient height for the second cart to be slid under it and be positioned, at least partially, under the circulation pump when the carts are nested.

The second cart has a platform provided with an upper face on which are positioned disposable components such as filter components and re-usable components such as a second pressure sensor. This second cart furthermore has storage drawers adapted to accommodate collecting bags for the liquid or other containers such as bags for sampling or drainage.

A pipe is linked to a source bag containing the liquid to treat and comprises a component adapted to cooperate with the pump to make that liquid flow towards the filter components, passing via the pressure sensors. Another pipe is connected to the filter component to make that treated liquid flow towards the collecting bag positioned within a drawer.

The diversity of the treatments that may be performed on this type of installation is great, in particular depending on the selection by the user of the liquid to treat and on the degree of purity to obtain for the collected treated liquid.

This great diversity in the treatments imposes the use of numerous re-usable and disposable components that are different from one treatment to another. In particular, the number of filter components and the means for control and actuation that are associated with these components and that are provided to measure and monitor the parameters of the treated liquid can increase. Therefore, the arrangement of these filter components and means for control and actuation are required to be simple, convenient and flexible.

SUBJECT OF THE INVENTION

The invention aims to provide an installation enabling the simple, convenient and economical implementation of treatments for biological liquid.

For this, the invention concerns an installation for treating biological liquid by chromatography, generally extending in a longitudinal direction and comprising:

- at least one supply valve for supplying biological liquid to treat, configured to be connected to at least one biological liquid supply container;
- at least one supply pump disposed downstream of said at least one supply valve and connected to the latter;
- a plurality of instrument members disposed downstream of said at least one supply pump, including at least one distribution valve and at least one device for measuring a physico-chemical parameter of the biological liquid, and which are connected to said at least one supply pump;
- at least one chromatography column disposed downstream of said plurality of instrument members and directly associated with and connected to at least some of them, and configured to be supplied with biological liquid by said at least one supply pump; and
- a plurality of single-use pipes configured to be connected to said at least one supply valve, to said at least one supply pump, to said plurality of instrument members and to said at least one chromatography column, so as to form at least one supply line for supplying biological liquid to treat of a treatment circuit of said installation;

characterized in that said instrument members associated with said at least one chromatography column are each mounted on at least one dedicated control and actuation platform, which extends in a vertical direction relative to the generally longitudinal direction of extension of said installation, and are disposed substantially above each other on said dedicated control and actuation platform.

The installation according to the invention presents an arrangement which ensures first of all a centralized setting in place of the instrument members directly associated with the chromatography column by positioning these latter on a single individual control and actuation platform.

What is more, such a substantially superposed arrangement of these instrument members on the vertical platform gives a particularly advantageous compactness in comparison to the installations in which the instrument members are instead scattered.

This compactness is all the more advantageous in the context of the invention since it enables the floor space (also called footprint area) occupied by the installation, which is required to be set up in what are referred to as clean rooms, with particularly severe sanitary constraints.

Furthermore, such a substantially superposed arrangement of the instrument members on the vertical platform facilitates the access to these instrument members and thus their connection in particular to the chromatography column and to the supply pump. It is also particularly easy to replace the vertical platform and its instrument members by another platform, or even to replace only one of the instrument members on that platform.

Such an arrangement thus provides simple and rapid mounting/demounting of the installation by facilitating the connections of the flexible pipes, or even by limiting the crossing of these pipes.

Furthermore, such an arrangement is particularly reproducible in case of increasing the number of chromatography columns and thus the number of associated instrument members, while maintaining high flexibility and access and while furthermore making it possible to significantly reduce the length of the disposable pipes of the treatment circuit. Thus, the volume of liquid inside the circuit of the installation is minimized. It will be noted that in this case, the installation generally comprises at least two pumps.

It therefore follows from the above that the installation for treatment of biological liquid according to the invention is particularly simple, convenient and economical.

According to other preferred simple, convenient and economical features of the installation according to the invention:

- said at least one control and actuation platform comprises several distribution valves and one or more measuring devices chosen from a conductivity sensor and/or a pH sensor and/or an air presence sensor;
- said distribution valves are each provided with a valve body and a valve head which extends from said body and which is provided to receive at least portions of pipes of said supply line, and said at least one control and actuation platform comprises a support block which extends vertically, in which are housed said valve bodies and from which said valve heads project laterally, as well as a support plate fastened to said support block and having an arm which projects from said support block and on which is mounted said at least one measuring device;
- the installation comprises several chromatography columns disposed downstream of said at least one control and actuation platform, and which extend in a direction generally transverse to said generally longitudinal direction of extension of said installation; it being possible for said chromatography columns to be preferably arranged in a triangle if there are at least three of them;
- the installation comprises several dedicated control and actuation platforms, each being individually associated with one of said chromatography columns, said dedicated control and actuation platforms being disposed in the same generally transverse direction as said chromatography columns;
- said control and actuation platforms are mounted on a first cart and said chromatography columns are mounted on a second cart configured to be juxtaposed against and/or partially nested with said first cart;
- said first cart comprises a first chassis, at least one electrical and pneumatic distribution cabinet mounted on said chassis and on which is disposed said at least one supply valve, at least one receiving space formed in said chassis and provided to receive containers for recovery of liquids, and at least one support plate mounted in a projecting manner on said chassis and on which are disposed said at least one supply pump and said control and actuation platforms, and said second cart comprises a second chassis provided with a support board provided to receive said chromatography columns and configured to come at least partially to nest under said plate of said first cart;
- the installation further comprises additional instrument supports disposed downstream of said chromatography columns and on which are mounted one or more additional measuring devices chosen from a conductivity sensor, and/or a pH sensor and/or a UV radiation sensor;

the additional instrument supports may be individually associated with one of said chromatography columns, and/or be disposed in the same generally transverse direction as said chromatography columns and said dedicated control and actuation platforms;

said additional instrument supports are mounted on a third cart configured to be juxtaposed against and/or partially nested with said first cart and/or with said second cart;

the installation further comprises a plurality of supplementary instrument members disposed downstream of said chromatography columns, including at least one outlet valve and at least one supplementary measuring device chosen from a pressure sensor and/or a spectrophotometer, said supplementary instrument members being mounted on said third cart, downstream of said additional instrument supports;

said third cart comprises a third chassis, substantially the shape of an inverted U, on which are mounted at least said additional instrument supports at a free end of said third chassis, and which is configured to be juxtaposed against said first chassis of said first cart by an opposite end to its free end, and to nestingly receive, in a space formed by the inverted U between its opposite end and its free end, said second chassis of said second cart provided with said chromatography columns;

said at least one supply valve and/or said at least one distribution valve are three-way valves, of which two ways are inlets and one an outlet or one an inlet and two outlets, and preferably a valve provided with a head having two reception channels for portions of said pipes, and a pinching mechanism configured to allow or prevent the passage of said biological liquid in said portions of said pipes received in the two said channels.

the installation further comprises a reserve container disposed downstream of said at least one chromatography column and connected to the latter, said reserve container being provided to receive a buffer product used for the cleaning of said at least one chromatography column after treatment of said biological liquid, and another supply valve disposed downstream of said reserve container and upstream of said at least one supply pump and connected to the latter, said other supply valve being configured to re-introduce, via said at least one supply pump, said buffer product into said supply line as liquid to treat in said at least one chromatography column;

the installation further comprises a plurality of inlet valves configured to be connected to containers for what are referred to as buffer products and to supply said treatment circuit for the purpose of preparing and/or cleaning and/or elution and/or regeneration of said at least one chromatography column, and at least one additional pump disposed downstream of said inlet valves and upstream of said at least one chromatography column and connected to these latter; pipes of said plurality of single-use pipes being configured to be connected to said inlet valves and to said additional pump, so as to form at least one additional line, which extends substantially longitudinally and in parallel to said supply line, from respectively said inlet valves and said at least one supply valve, to said at least one dedicated control and actuation platform; and/or the installation further comprises other instrument members, among which are, on said supply line:
a product presence sensor disposed upstream of said at least one supply valve; and/or
a two-way isolating valve and/or a flow meter disposed between said at least one supply valve and said at least one supply pump; and/or
a pressure sensor with or without a safety feature, and/or at least one drain valve, and/or at least two debubbler valves and a debubbler connected to each of these debubbler valves and/or at least one filter valve and a filter connected to said at least one filter valve, which are disposed between said at least one supply pump and said at least one control and actuation platform; and/or on said additional line:
a two-way isolating valve and/or a flow meter disposed between said inlet valves and said at least one additional pump; and/or
at least one pressure sensor with or without a safety feature, and/or at least one drain valve, and/or at least two debubbler valves and a debubbler connected to each of those debubbler valves, disposed between said additional pump and said at least one control and actuation platform.

BRIEF DESCRIPTION OF THE DRAWINGS

The disclosure of the invention will now be continued with the description of embodiments, given below by way of illustrative and non-limiting example, with reference to the accompanying drawings, in which:

FIGS. 4 to 8 are views of the installation in its configuration illustrated in FIG. 3, which are respectively a front view, a three-quarter view from the back, side views and a plan view;

FIG. 12 is a diagrammatic view of a circuit for biological liquid treatment by chromatography, implemented in the installation illustrated in FIGS. 1 to 8.

DETAILED DESCRIPTION OF AT LEAST ONE EMBODIMENT

Figure 1:
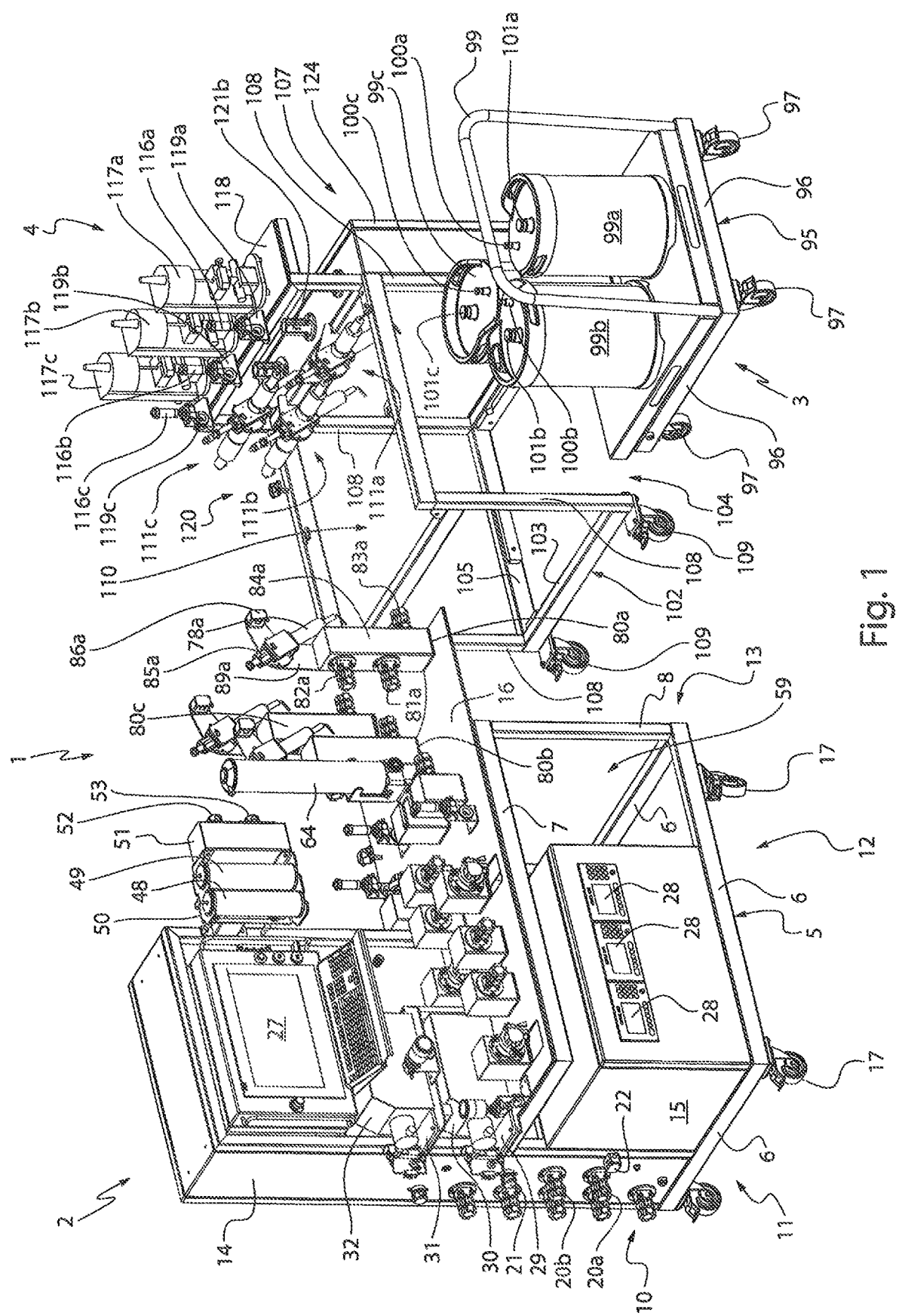
FIGS. 1 to 3 represent, diagrammatically in perspective, a treatment installation in accordance with the invention, viewed from different angles and in different configurations of assembly.
Figure 2:
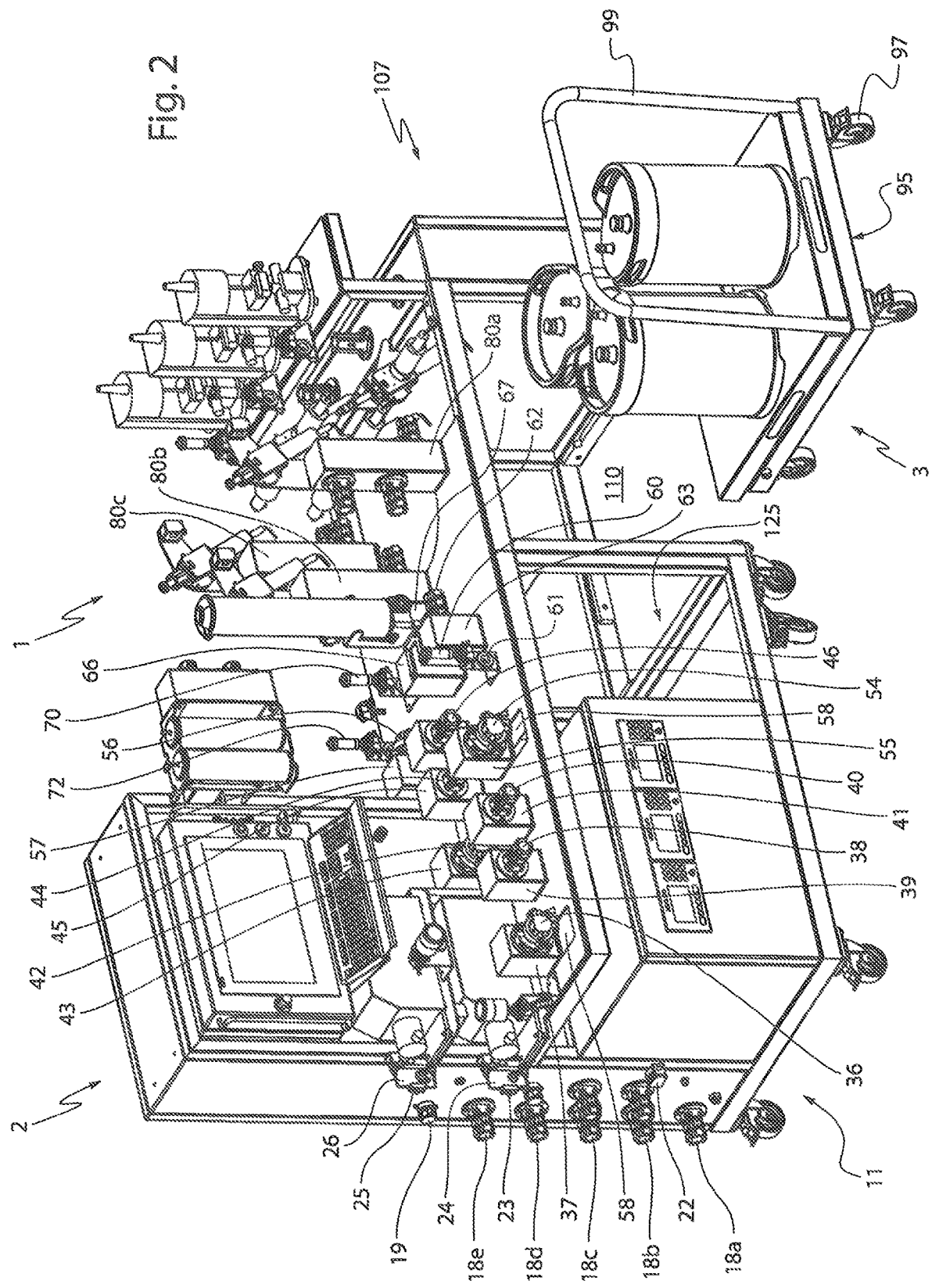
Figure 3:
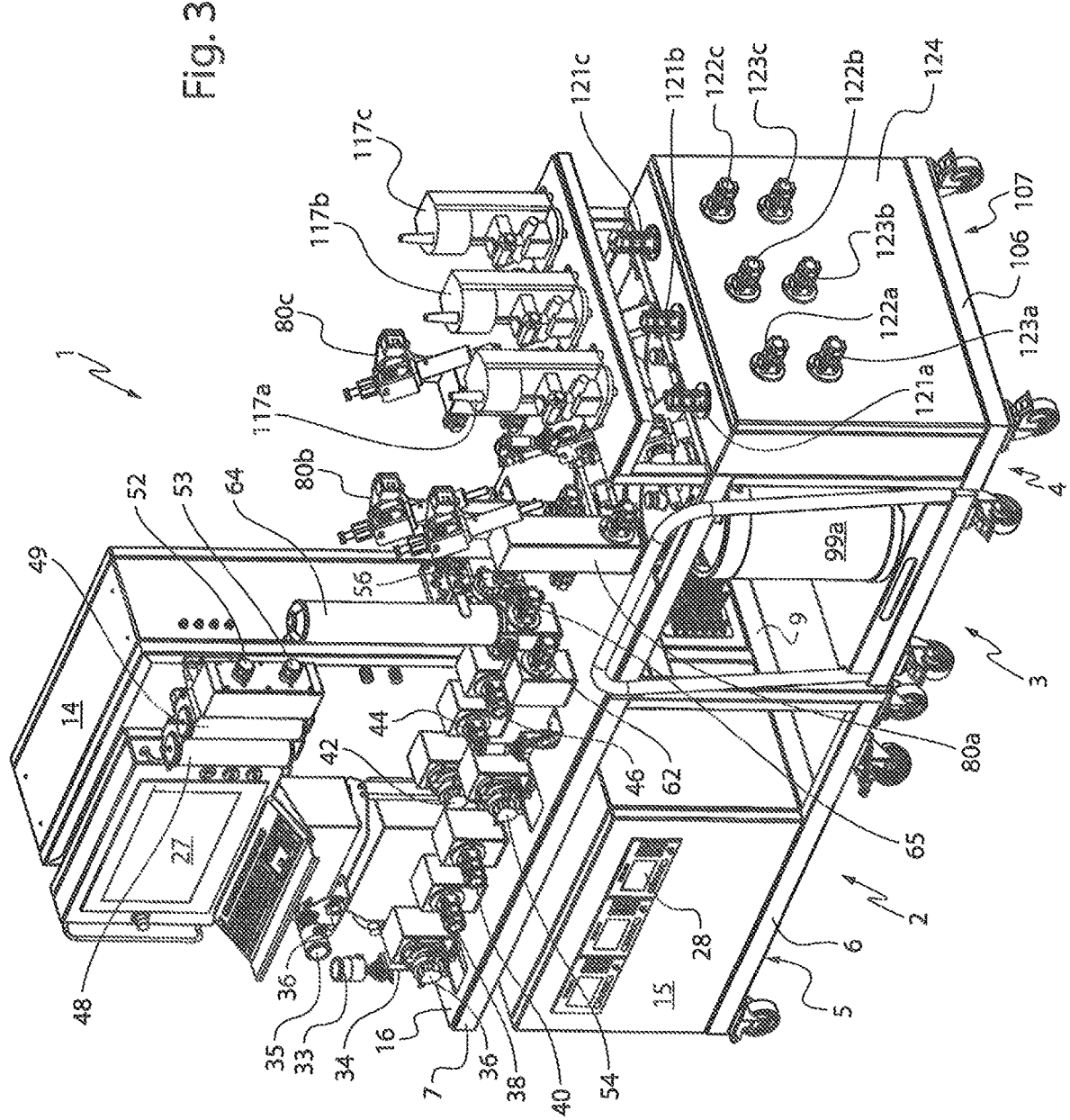
Figure 4:
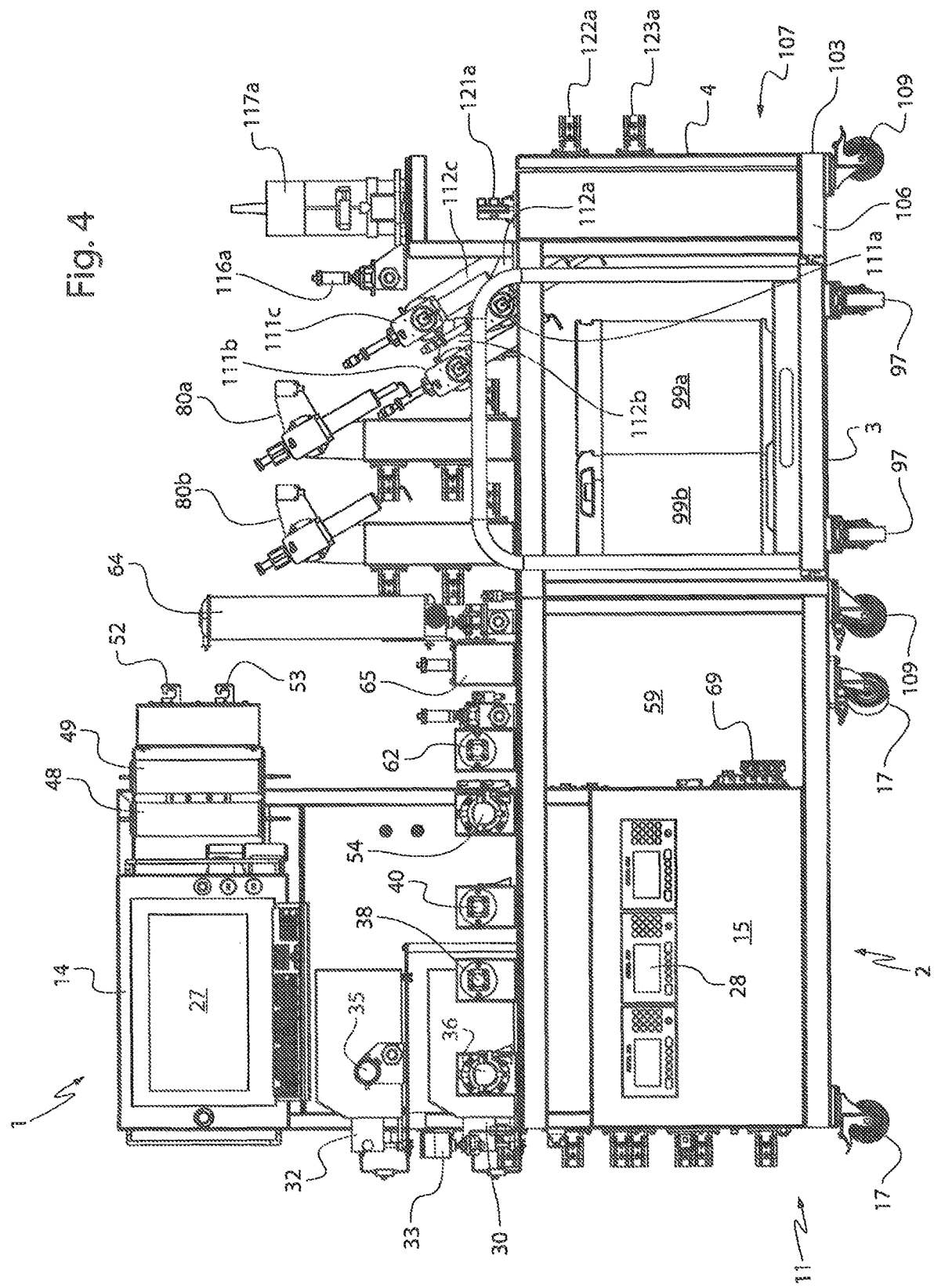

FIGS. 1 to 3 illustrate an installation 1 for treatment by chromatography, in different assembly configurations.

The installation 1 here comprises a first cart 2, a second cart 3 as well as a third cart 4, which are configured to be juxtaposed and at least partially nested in each other.

In FIG. 1, the first, second and third carts 2 to 4 are separated and at a distance from each other. The first and third carts 2 and 4 are arranged in the same longitudinal direction whereas the second cart 3 is located offset, in front of the third cart 4.

RECTIFIED SHEET (RULE 91) ISA/EP

In FIG. 2, the first and third carts 2 and 4 are juxtaposed and nested along the longitudinal direction of extension of the installation 1, whereas the second cart 3 is still located offset in front of the third cart 4.

In FIG. 3, the second cart 3 is partially nested in the third cart 4 and located in immediate proximity to the first cart 2 such that this second cart 3 is also partially nested with and juxtaposed against the first cart 2.

Figure 8:
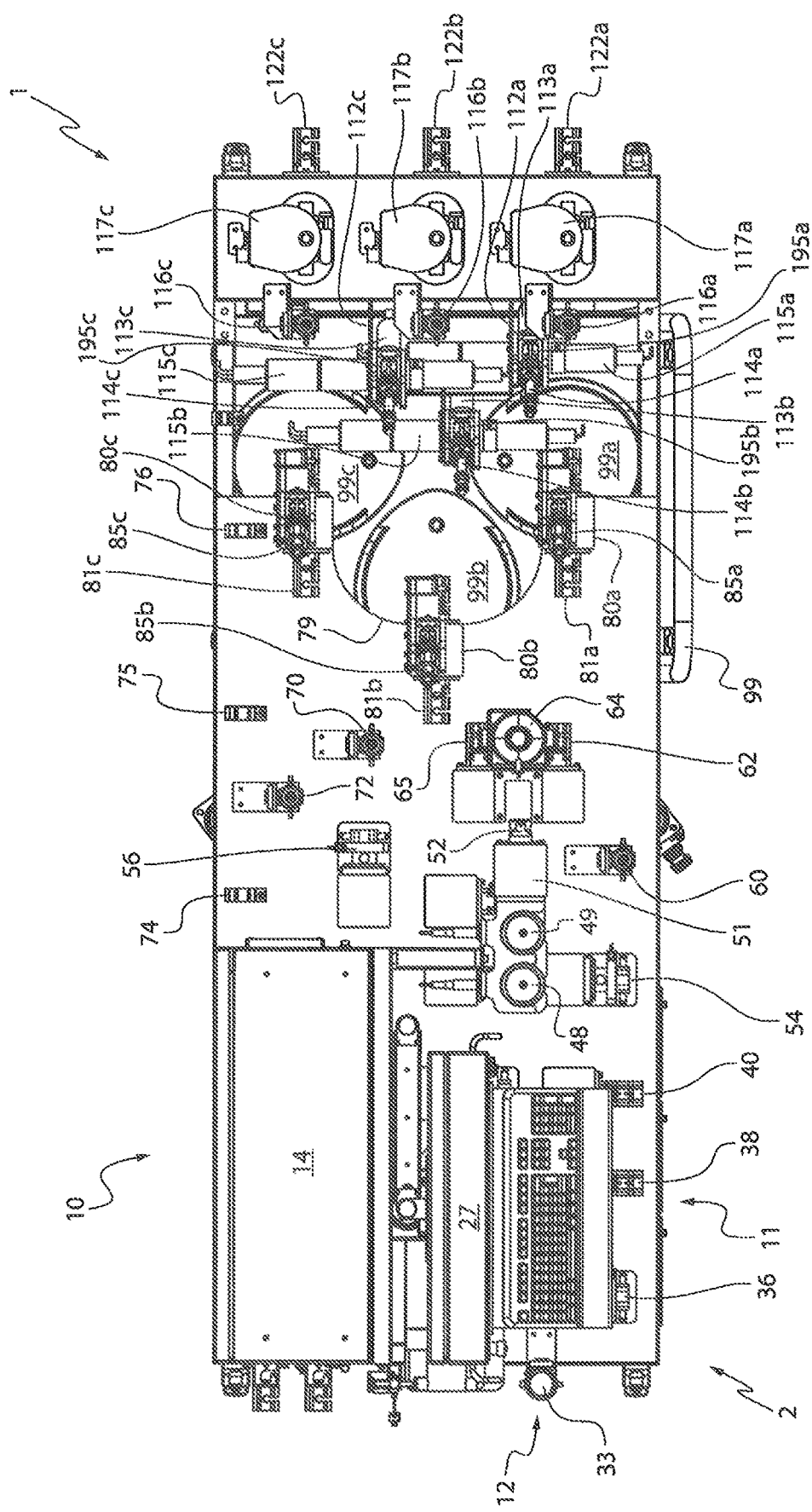
Figure 9:
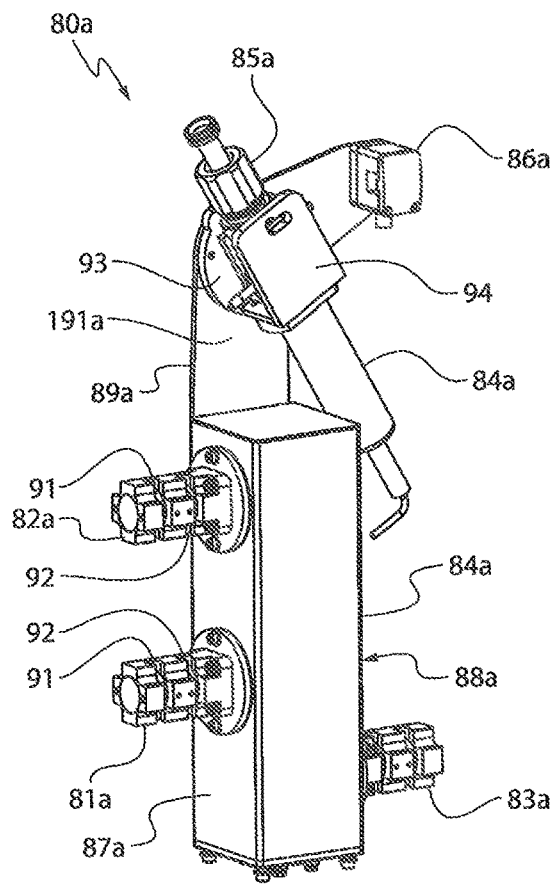
FIGS. 9 to 11 represent, diagrammatically in perspective, a control and actuation platform of the installation illustrated in the preceding Figures, viewed from different angles.
Figure 10:
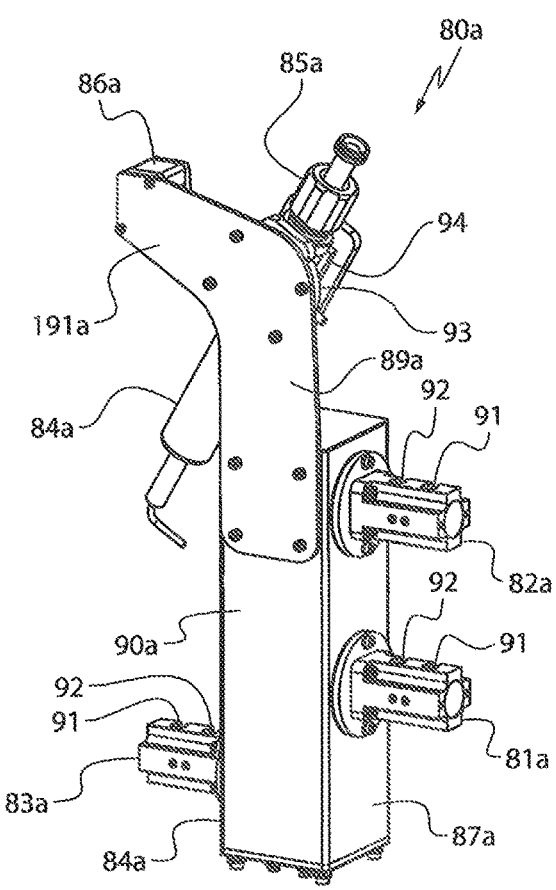
Figure 11:
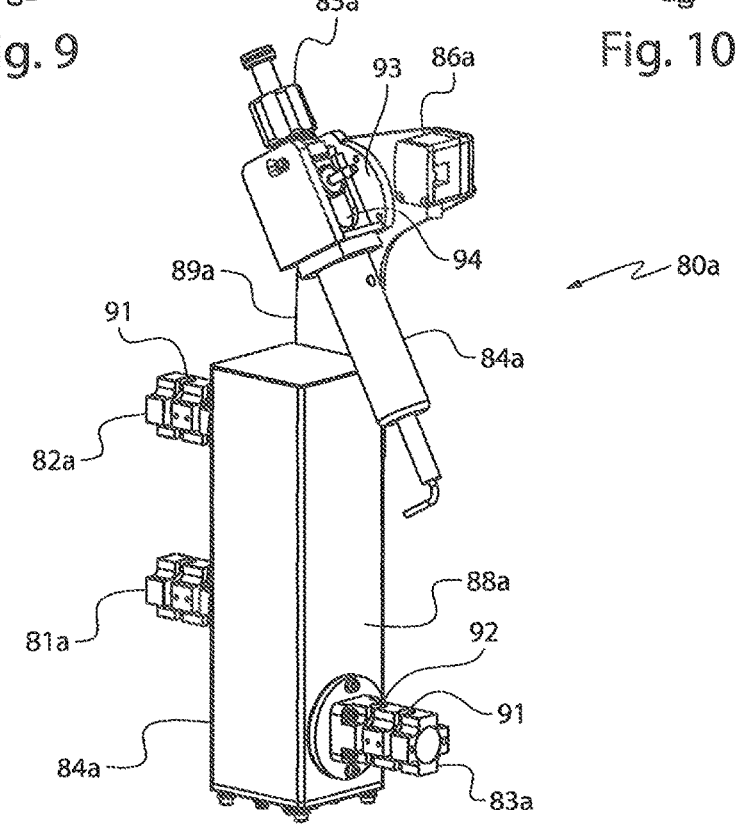

A detailed description will now be given of the structure of each of the first, second and third carts 2 to 4 and of the components they carry, with reference to FIGS. 1 to 11, in which FIGS. 4 to 8 are respectively a front view, a three-quarter view from the back, side views and a plan view of the installation 1 with its first, second and third carts 2 to 4 assembled, and in which FIGS. 9 to 11 represent a control and actuation platform of the installation.

The first cart 2 is provided with a first metal chassis 5 having a first lower frame 6 here substantially rectangular, a first upper frame 7 here hexagonal, substantially L-shaped, and situated partially facing and at a distance from the first lower frame 6, and several vertical uprights 8 connected to the first lower and upper frames 6 and 7 so as to form a rigid first chassis 5.

The first lower frame 6 is mounted here on four castors to facilitate its transport.

Each of the first lower and upper frames 6 and 7 is formed of longitudinal bars, also called longerons, extending in a longitudinal direction, and transverse bars, also called cross-members, extending in a transverse direction, here substantially at a right angle to the longitudinal direction. The first lower frame 6 is furthermore formed from an intermediate cross-member 9 disposed between its two transverse bars and attached to its two longitudinal bars.

The first cart 2 carries a main electrical and pneumatic distribution cabinet 14 mounted on the first lower frame 6, on the back 10 and on the first side 11 of the first cart 2, a secondary cabinet 15 also mounted on the first lower frame 6, but instead on the front 12 and on the first side 11 of the first cart 2. The secondary cabinet 15 is thus disposed in front of the main cabinet 14.

The main cabinet 14 extends generally vertically, which means that it is higher than it is long, from the first lower fame 6 and beyond the first upper frame 7, whereas the secondary cabinet 15 extends generally longitudinally, which means that it is longer than it is high, between the first lower and upper frames 6 and 7, from the transverse bar situated on the first side 11 of the first lower frame 6 to its intermediate cross-member 9.

The first cart 2 furthermore carries a support plate 16 mounted on the first upper frame 7 and projecting from the latter over a second side 13 of the first cart 2, which is an opposite side to its first side 11; such that a portion of the support plate 16 overhangs beyond the first chassis 5.

It will be noted that the support plate 16 here has a substantially L-shaped contour to conform to the contour of that first upper frame 7, and is provided with a recess to enable the passage of the main cabinet 14.

The support plate 16 is configured to receive reusable components of the treatment installation 1 and support means not only for these reusable components but also for the disposable components of that installation 1.

In particular here, the installation 1 comprises a plurality of supply valves disposed on the first side 11 of the first cart 2 and partially housed in a lateral face of the main cabinet 14, in two distinct rows.

The row situated furthest to the back 10 of the first cart 2 has five superposed three-way valves 18a to 18e and one two-way isolation valve 19 situated above the five three-way valves 18a to 18e; whereas the other row has two superposed three-way valves 20a and 20b and a two-way isolation valve 21 situated above the two three-way valves 20a and 20b (FIGS. 2 and 7). It will be noted that the isolation valves 19 and 21 are configured here to have either on/off operation, or proportional operation.

It will be noted that each of the valves 18 and 20 has a body housed in the main cabinet 14 and a head extending the body and projecting from the main cabinet 14 on the first side 11 of the first cart 2.

Furthermore, each of the valves 18 to 20 is configured to be connected by disposable flexible pipes to containers having determined products.

In particular, the valves 20a to 20b are supply valves configured to be connected to containers of biological liquid to treat by chromatography and form the start of a supply line of a circuit for treatment by chromatography of the installation 1.

For this, the valve 20a is here configured to be connected to a container of equilibration buffer product and to what is referred to as a reserve container of liquid to retreat, and the valve 20b is configured here to be connected to the valve 20a and to a container of biological liquid to treat.

As regards the valve 21 this is a proportional valve here configured to be connected to the valve 20b as well as to the rest of the supply line extending downstream of the valves 20a, 20b and 21.

What is more, the valves 18a to 18e are inlet valves configured to be connected to containers of what are referred to as buffer products and to supply a treatment circuit of the installation for the purpose of preparing and/or cleaning and/or eluting and/or regenerating chromatography columns and form the start of an additional line of the circuit for treatment by chromatography of the installation 1.

For this, the valve 18a is configured here to be connected to a container for equilibration buffer product and to a container for first washing buffer product, the valve 18b is configured here to be connected to the valve 18a and to a container of second washing buffer product, the valve 18c is configured here to be connected to the valve 18b and to a container for eluting buffer product, the valve 18d is configured here to be connected to the valve 18c and to a container for cleaning product, and the valve 18e is configured here to be connected to the valve 18d and to a container for regenerating buffer product.

As regards the isolation valve 19 this is a distribution valve here configured to be connected to the valve 18e as well as to the rest of the additional line extending downstream of the valves 18a to 18b and 19.

The installation 1 comprises an air presence sensor 22 here fastened to a vertical upright 8 on the first side 11 of the first cart 2 and in immediate proximity to the supply valve 20a The air presence sensor 22 is configured here to be connected to a portion of pipe between the container for biological liquid and the supply valve 20b and makes it possible to detect the presence and/or the absence of product.

The installation 1 comprises a first flow meter 23 mounted via a fastening bracket 24 on a vertical upright 8 on the first side 11 of the first cart 2. This first flow meter 23 is configured to be connected on the supply line, upstream, to the isolation valve 21.

The installation 1 comprises a second flow meter 25 mounted via a fastening bracket 26 on the same vertical upright 8 on the first side 11 of the first cart 2. This second flow meter 25 is configured to be connected on the additional line, upstream, to the isolation valve 19.

The installation 1 comprises a main system for data processing 27 fastened to the main cabinet 14 and which is formed here by a computer provided with a keyboard and a monitor which are accessible from the front 12 of the first cart 2, as well as a second data processing system 28 here formed by several actuation and control panels housed in the secondary cabinet and also accessible from the front 12 of the first cart 2.

It will be noted that the main cabinet 14 is provided with actuation buttons 68 on a back face at the back 10 of the first cart 2 and with pneumatic and electrical connectors 69 provided on a lateral face of that cabinet 14, which is an opposite face to the lateral face from which project the valves 18a to 18e, 19, 20a, 20b and 21.

The installation 1 comprises a first pump support 29 fastened on the front of the main cabinet 14 and on which is mounted a supply pump 30, as well as a second pump support 31 also fastened on the front of the main cabinet 14 and on which is mounted an additional pump 32.

The supply pump 30 is configured here to be connected on the supply line downstream of the supply valves 20a and 20b isolation valve 21 and is provided with a pump head disposed opposite the first flow meter 23 and connected to the latter; whereas the additional pump 32 is configured here to be connected on the additional line downstream of the inlet valves 18a to 18e and isolation valve 19 and is provided with a pump head disposed opposite the second flow meter 25 and connected to the latter. These pumps 30 and 32 are for example of diaphragm type and are configured to cause the products present in the containers connected to the valves 18a to 18e, 20a and 20b to flow according to the state of these latter.

The installation 1 comprises a first pressure sensor with a safety member 33 mounted, via a fastening bracket 34, on the support plate 16, on the first side 11 of the first cart 2; as well as a second pressure sensor with a safety member 35 mounted, via a fastening bracket 36, on the second pump support 31.

The first pressure sensor with a safety member 33 is configured here to be connected on the supply line downstream of the supply pump 30; whereas the second pressure sensor with a safety member 35 is configured here to be connected on the additional line downstream of the additional pump 32.

The first and second pressure sensors with a safety member 33 and 35 are each configured to measure the pressure of the liquid flowing in the respective line of the treatment circuit and to stop the respective pump beyond a certain threshold pressure value.

The installation 1 comprises a first drain valve 36 provided with a body housed in a support block 37 mounted on the support plate 16, on the side of the supply pump 30 towards the front 12 of the first cart 2, and with a head extending the body and projecting from the support block. This first drain valve 36 is configured here to be connected on the supply line, upstream, to the supply pump 30 and, downstream, in particular to a waste container.

The installation 1 comprises a first debubbler valve 38 provided with a body housed in a support block 39 mounted on the support plate 16, beside the first drain valve 36 towards the second side 13 of the first cart 2, and with a head extending the body and projecting from the support block. This first debubbler valve 38 is configured here to be connected, on the supply line, upstream, to the first drain valve 36 and, downstream, in particular to a first debubbler 48 (see below).

The installation 1 comprises a second debubbler valve 40 provided with a body housed in a support block 41 mounted on the support plate 16, beside the first debubbler valve 38 towards the second side 13 of the first cart 2, and with a head extending the body and projecting from the support block. This second debubbler valve 40 is configured here to be connected, on the supply line, upstream, to the first debubbler valve 38 and to the first debubbler 48.

This first debubbler 48 is mounted, via a fastening bracket 50, on a vertical upright 8 of the first chassis 5, on an opposite side of the main cabinet 14 to the supply and inlet valves, and rather on the second side 13 of the first cart. This first debubbler 48 is configured here to be connected, as inlet connection, to the first debubbler valve 38, as main outlet connection, to the second debubbler valve 40 and, as secondary outlet connection, to a first venting valve 52.

This first venting valve 52 is provided with a body housed in a support block 51 fastened to the fastening bracket 50, and with a head extending the body and projecting from the support block. This first venting valve 52 is configured here to open to the atmosphere.

The installation 1 comprises a second drain 42 provided with a body housed in a support block 43 mounted on the support plate 16, to the rear of the supply pump 30 and towards the second side 13 of the first cart 2, and with a head extending the body and projecting from the support block. This second drain valve 42 is configured here to be connected on the additional line, upstream, to the additional pump 32 and, downstream, in particular to a waste container.

The installation 1 comprises a third debubbler valve 44 provided with a body housed in a support block 45 mounted on the support plate 16, beside the second drain valve 42 towards the second side 13 of the first cart 2, and with a head extending the body and projecting from the support block. This third debubbler valve 44 is configured here to be connected, on the additional line, upstream, to the second drain valve 42 and, downstream, in particular to a second debubbler 49 (see below).

The installation 1 comprises a fourth debubbler valve 46 provided with a body housed in a support block 47 mounted on the support plate 16, beside the third debubbler valve 44 towards the second side 13 of the first cart 2, and with a head extending the body and projecting from the support block. This fourth debubbler valve 46 is configured here to be connected, on the additional line, downstream, to the third debubbler valve 44 and to the second debubbler 49.

This second debubbler 49 is mounted, via the fastening bracket 50, on the vertical upright 8 of the first chassis 5, on the opposite side of the main cabinet 14 to the supply and inlet valves, and rather on the second side 13 of the first cart. This second debubbler 48 is configured here to be connected, as inlet connection, to the third debubbler valve 44, as main outlet connection, to the fourth debubbler valve 46 and, as secondary outlet connection, to a second venting valve 53.

This second venting valve 53 is provided with a body housed in the support block 51 fastened to the fastening bracket 50, and with a head extending the body and projecting from the support block. This second venting valve 53 is configured here to open to the atmosphere.

The installation 1 comprises a third drain valve 54 provided with a body housed in a support block 55 mounted on the support plate 16, beside the second debubbler valve 40 towards the second side 13 of the first cart 2, and with a head extending the body and projecting from the support block. This third drain valve 54 is configured here to be connected on the supply line, upstream, to the second debubbler valve 40 and, downstream, in particular to a waste container.

The installation 1 further comprises a fourth drain valve 56 provided with a body housed in a support block 57 mounted on the support plate 16, beside the fourth debubbler valve 46 towards the back 10 of the first cart 2, and with a head extending the body and projecting from the support block. This fourth drain valve 56 is configured here to be connected on the additional line, upstream, to the fourth debubbler valve 46 and, downstream, in particular to a waste container.

It will be noted that windows 58 are provided in the support plate 16 under the drain valves 36, 42, 54 and 56 to enable portions of pipe of the treatment circuit to be passed towards the waste containers which may be housed for example in a receiving space 59 provided between the first lower and upper frames 6 and 7 and between the secondary cabinet 15 and the second side 13 of the first chassis 5.

The installation 1 comprises a third pressure sensor 60, here without a safety feature, mounted via a fastening lug 61 here S-shaped on the support plate 16, beside the third drain valve 54 towards the second side 13 of the first cart 2. The third pressure sensor 60 is configured here to be connected to the supply line downstream of the third drain valve 54.

The installation 1 comprises a first filter valve 62 provided with a body housed in a support block 63 mounted on the support plate 16, beside the third pressure sensor 60 towards the second side 13 of the first cart 2. The first filter valve 62 is configured here to be connected on the supply line, upstream, to the third pressure sensor 60 and, downstream, to a filter 64 (see below).

The installation 1 comprises a second filter valve 65 provided with a body housed in a support block 66 mounted on the support plate 16, beside the first filter valve 62 towards the back 10 of the first cart 2. The second filter valve 65 is configured here to be connected on the supply line, upstream, to the filter 64 and the first filter valve 62.

This filter 64 is mounted, via a fastening bracket 67 mechanically connected to the top of the support blocks 63 and 66 respectively of the first and second filter valves 62 and 65, substantially above these first and second filter valves 62 and 65. This filter 64 is configured here to be connected, as inlet connection, to the first filter valve 62, and as outlet connection, to the second filter valve 65.

Figure 5:
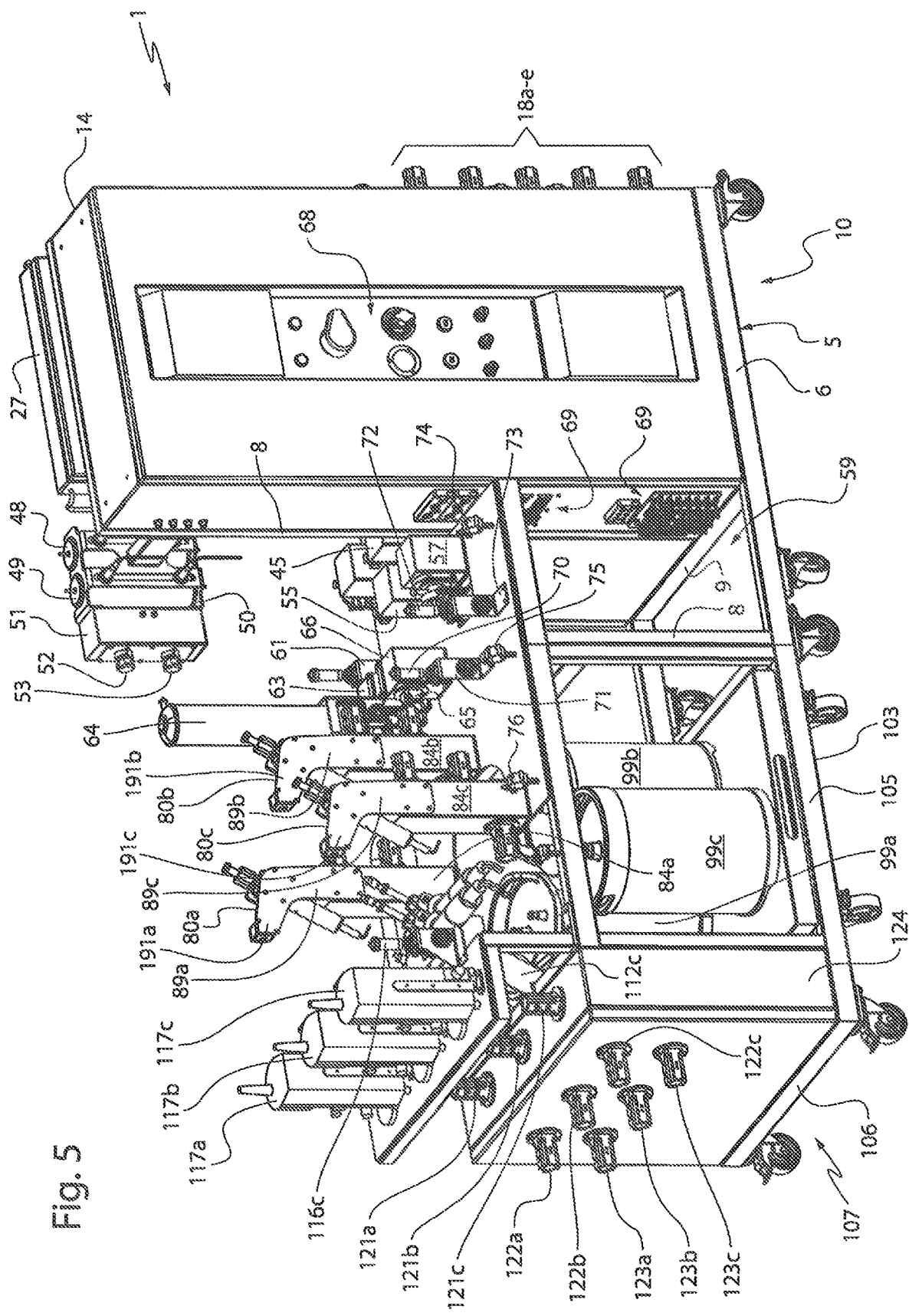

The installation 1 comprises a fourth pressure sensor 70, here without safety feature, mounted via a fastening lug 71 here S-shaped on the support plate 16, near the second filter valve 65 towards the back 10 of the first cart 2; as well as a fifth pressure sensor 72 here without safety feature and which is mounted, via a fastening bracket 73 here S-shaped, on the support plate 16 near the fourth drain valve 56 and the fourth pressure sensor 70, towards the back 10 of the first cart 2 (FIGS. 5 and 8).

The fourth pressure sensor 70 is configured here to be connected on the supply line, upstream, to the second filter valve 65; whereas the fifth pressure sensor 72 is configured here to be connected on the additional line, upstream, to the fourth drain valve 56.

The installation 1 further comprises a cable raceway formed by collars 74 to 76 provided for conveying electric and pneumatic cables (not shown) which run along a back edge of the support plate 16, from the face of the main cabinet 14 where the connectors 69 are located towards the second side 12 of the first cart 2 and beyond to reach the overhanging portion of the support plate 6 (FIGS. 5 and 8). These cables enable the instrument members of the installation to be supplied.

It will be noted that the drain valves 36, 42, 54 and 56 are three-way valves with an inlet aperture and two outlet apertures, including the drain outlet aperture which is either open or closed whereas the inlet aperture and the other outlet aperture are always open; and the debubbler valves 38, 40, 44 and 46 and the filter valves 62 and 65 are three-way valves similar to the supply valves 20*a* and 20*b* and to the inlet valves 18*a* to 18*e*, of a type different from the drain valves (see below).

It will also be noted that the components described above in relation with the first cart 2 are located substantially within the occupied floor space defined by the first chassis 5. In other words, with the exception of the collar 76, these components are not disposed on the overhanging portion of the support plate 16.

Furthermore, these components are diagrammatically illustrated in the first part of FIG. 12 (sheet 9/10 of the drawings) and mainly form instrument members (the valves and various sensors), among which are devices for measuring physico-chemical parameters (the various sensors) of the liquids passing in the treatment circuit, in the supply and additional lines.

The installation 1 further comprises three dedicated control and actuation platforms 80*a*, 80*b* and 80*c*, mounted on the overhanging portion of the support plate 6, which each extend in the vertical direction relative to the generally longitudinal direction of extension of the first cart 2, and which are disposed on the support plate 16 in a generally transverse direction to the generally longitudinal direction of extension of the first cart 2.

In particular, the three platforms 80*a*, 80*b* and 80*c* are arranged substantially in a triangle, around a cut-out 79 formed at one end of the portion of the support plate 16 which overhangs.

As the platforms 80*a*, 80*b* and 80*c* are identical, only one will be described in detail, which is platform 80*a*, knowing that this description applies to each of the other platforms 80*b* and 80*c*, in particular with reference to FIGS. 9 to 11.

Platform 80*a* comprises instrument members, including three distribution valves 81*a*, 82*a* and 83*a*, each provided with a body and a head extending the body, and several measuring devices including a conductivity sensor 78*a*, a pH sensor 85*a* and an air presence sensor 86*a*.

Platform 80*a* comprises a support block 84*a* here of substantially parallelepiped shape, which extends vertically, and in which are housed the body of the valves 81*a*, 82*a* and 83*a* and from which the heads of the valves 81*a*, 82*a* and 83*a* project laterally.

In particular, the heads of the valves 81*a* and 82*a* project from a first lateral face 87*a* of the support block 84*a* here turned towards the first side 11 of the first cart 2, whereas the head of the valve 83*a* projects from a second lateral face 88*a* of the support block 84*a* turned towards the second side 13 of the first cart 2.

Platform 80*a* further comprises a support plate 89*a* fastened to a third lateral face 90*a* of the support block 84*a*, turned towards the back 10 of the first cart 2, and having an arm 191*a* which projects from the support block 84*a* and on which are mounted the sensors of conductivity 78*a*, pH 85*a* and air presence 86*a*.

In particular, the air presence sensor 86*a* is directly mechanically connected to a free end of the arm 191*a* whereas the sensors of conductivity 78*a* and pH 85*a* are mounted with partial insertion in a fluid chamber 94, which chamber is fastened on a flange 93 itself mechanically connected to the arm 191*a*, between its free end where the air presence sensor 866*a* is fastened and the portion of the support plate 89*a* fastened on the third lateral face 90*a* of the support block 84*a*.

This fluid chamber 94 here forms an integral part of the supply line of the treatment circuit and has two chamber connectors which are for example male for the connection of portions of pipes, one of the chamber connectors being directed towards the support block 84*a* and the other of the chamber connectors being directed towards the air presence sensor 86*a*.

Valve 83*a*, valve 81*a*, valve 82*a*, the conductivity sensor 78*a*, the air presence sensor 86*a* and the pH sensor 85*a* are disposed substantially above each other on the dedicated control and actuation platform 80*a*.

Each of the valves 81*a*, 81*b* and 81*c* is configured here to be connected, on the supply line, upstream, to the fourth pressure sensor 70 and, downstream, to the respective valve 82*a*, 82*b* and 82*c*.

Each of the valves 81*a*, 81*b* and 81*c* is furthermore configured here also to be connected, on the additional line, upstream, to the fifth pressure sensor 72 and, downstream, to the respective valve 82*a*, 82*b* and 82*c*.

Each valve 82*a*, 82*b* and 82*c* is configured here to be connected, on the supply line, upstream, to the respective valve 81*a*, 81*b* and 81*c*, and, downstream, at the same time to the respective pH sensor 85*a*, 85*b* and 85*c* and to the respective conductivity sensor 78*a*, 78*b* and 78*c*.

Each of the pH sensors 85*a*, 85*b* and 85*c* and conductivity sensors 78*a*, 78*b* and 78*c* is thus configured here to be connected on the supply line, upstream, to the respective valve 82*a*, 82*b* and 82*c* and, downstream, to the respective air presence sensor 86*a*, 86*b* and 86*c*.

Each air presence sensor 86*a*, 86*b* and 86*c* is configured here to be connected, upstream, at the same time to the respective pH sensor 85*a*, 85*b* and 85*c* and to the respective conductivity sensor 78*a*, 78*b* and 78*c* and, downstream, to the respective valve 83*a*, 83*b* and 83*c*.

Each of the valves 83*a*, 83*b* and 83*c* is configured here to be connected, on the supply line, upstream, to the respective air presence sensor 86*a*, 86*b* and 86*c* and, downstream, in particular to a respective waste container and to a respective chromatography column (see below).

It will be noted that the distribution valves 81*a-c*, 82*a-c* and 83*a-c* are similar valves here to the filter valves 62 and 65, to the supply valves 20*a* and 20*b* and to the inlet valves 18*a* to 18*e*.

As explained above, all these valves are provided with a valve body and with a valve head which extends from the body, which valve head is provided here to receive portions of pipes of the respective line (supply or additional) where the respective valve is located.

In particular, with reference to FIGS. 9 to 11, valve 81*a* is a three-way valve, of which two ways are inlets and one an outlet or one an inlet and two outlets, provided with two channels 91 and 92 open at their ends, formed in the head, and configured to receive portions of pipes, and here a pinch mechanism configured to allow or prevent the passage of liquid in the portions of pipes received in the two channels 91 and 92, by pinching one or other of these latter. This pinching mechanism is housed in the head, between the two channels 91 and 92, and is actuated by a pneumatic actuator housed in the valve body. These are multi-tube pinch valves.

The other valves 81*b-c*, 82*a-c*, 83*a-c*, 18*a-e*, 20*a-b*, 62 and 65 here have a similar structure to that of valve 81*a*.

As a variant, the aforementioned three-way valves could be of a type other than that of the so-called pinch valves.

The second cart 3 is provided with a second metal chassis 95 having a second lower frame 96 here substantially rectangular, mounted on castors 97, a support board placed on that lower frame 96 and a maneuvering handle of inverted U-shape, which projects from the second lower frame 99, and which is provided to guide the transportation of the second cart 96.

It will be noted that the second lower frame 96 is formed from two longitudinal bars, also called longerons, extending in a longitudinal direction, and from two transverse bars, also called cross-members, extending in a transverse direction, here substantially at a right angle to the longitudinal direction. Here, the cross-members and longerons of the second lower frame 96 have substantially the same dimensions.

The installation 1 comprises several chromatography columns 99*a-c*, here three in number, which are placed on the support board in an arrangement, here triangular, enabling these columns to extend in a generally transverse direction to the generally longitudinal direction of extension of the installation. In other words, the three columns 99*a*, 99*b* and 99*c* extend within the length of cross-members rather than within the length of the longerons of the second lower frame 96.

These columns 99*a-c* are each provided, on an upper face, with an inlet connector 100*a-c* and with an outlet connector associated with a manual valve 101*a-c*.

These columns 99*a*, 99*b* and 99*c* are configured here to be connected, on the supply line, upstream, respectively to the distribution valves 83*a*, 83*b* and 83*c* at the location of their respective inlet connector 100*a-c*.

As regards the third cart 4, this is provided with a third metal chassis 102, of substantially inverted U-shape, having a third lower frame 103 of which a first part 105 is substantially C-shaped here and open to the front 104 of the third cart 4, and a second part 106 here substantially rectangular and juxtaposed against the first part 105 on a first free side 107 (or end) of the third cart 4.

The third cart 4 is furthermore provided with vertical uprights 108 connected to the third lower frame 102 and linked to each other, on the top of the third chassis 102, via two longitudinal bars, or longerons, extending in a longitudinal direction, and via two transverse bars, or cross-members, extending in a transverse direction, here substantially orthogonal to the longitudinal direction.

The third lower frame 102 too is mounted on four castors 109 to facilitate its transport.

The inverted U-shape of the third chassis 102 is provided to form a receiving space 110 so as to receive the second cart 3 (see below).

The installation 1 comprises additional instrument supports 111*a-c*, here three in number, disposed downstream of the columns 99*a-c* and each being dedicated to a chromatography column.

These additional instrument supports 111*a*, 111*b* and 111*c* are mounted on the third cart 4, via respective fastening brackets 112*a*, 112*b* and 112*c* which are fastened, directly or indirectly, to a transverse bar of the third chassis 102, on the first free side 107 of the third cart 4.

In particular, here, the fastening brackets 112*a* and 112*c* are bent and directly mechanically connected to the third chassis 102, whereas the fastening bracket 112*b* is mechanically connected to an intermediate tube (not shown) itself fastened directly to dedicated lugs of the brackets 112*a* and 112*c*.

Thus, the additional instrument supports 111*a*, 111*b* and 111*c* are disposed on the third cart 4 in a triangular general arrangement and along the transverse direction.

The installation 1 comprises several additional measuring devices carried by each of these additional instrument supports 111*a*, 111*b* and 111*c*, among which are respectively conductivity sensors 113*a*, 113*b* and 113*c*, pH sensors 114*a*, 114*b* and 114*c* and UV radiation sensors 115*a*, 115*b* and 115c, each being mounted, by group of three distinct sensors, on a respective fastening bracket 112a, 112b and 112c.

In particular, each of these sensors 113a-c, 114a-c and 115a-c is mounted with partial insertion in a fluid chamber 195a, 195b and 195c, substantially similar to that described above, which is fastened to a flange here centrally holed (not shown) which is itself mechanically connected to the respective bracket.

The conductivity sensors 113a-c and the pH sensors 114a-c are arranged in rather similar manner to those described above concerning platforms 80a-c, that is to say substantially vertically and respectively one opposite the other.

As regards the UV radiation sensors 115a-c, these are arranged substantially perpendicularly to the conductivity sensors 113a-c and to the pH sensors 114a-c on each respective additional instrument support 111a-c, on opposite sides of the fluid chamber and the holed flange, which is holed so as to enable the light rays to pass from an emitter to a receiver while passing through the fluid chamber, and thereby enable the measurement of the UV radiation.

The fluid chamber on each additional instrument support here forms an integral part of the supply line of the treatment circuit and has two chamber connectors for example male for the connection of portions of pipes.

Each of the conductivity sensors 113a-c, pH sensors 114a-c and UV radiation sensors 115a-c is configured here to be connected on the supply line, upstream, to the outlet connector associated with the respective manual valve 101a, 101b and 101c.

The installation 1 further comprises a plurality of supplementary instrument members, among which are pressure sensors 116a, 116b and 116c, here without safety feature, and optionally spectrophotometers 117a, 117b and 117c.

The spectrophotometers 117a, 117b and 117c are placed on a shelf 118 which is mounted in a raised location relative to the third chassis 102 and is mechanically connected to the longitudinal bars of that third chassis 102, which are situated on the front 104 and on the back 120 of the third cart 4.

The pressure sensors 116a, 116b and 116c are mounted on that shelf 118, via respective fastening lugs 119a, 119b and 119c which are directly mechanically fastened to that shelf 118.

The shelf 118 extends generally in the transverse direction and the spectrophotometers 117a-c and pressure sensors 116a-c are thus disposed along that same transverse direction.

Each pressure sensor 116a, 116b and 116c is configured to be connected, upstream, to the fluid chamber of a respective additional instrument support 111a-c to be connected both to a respective conductivity sensor 113a-c, to a respective pH sensor 114a-c and to a respective UV radiation sensor 115a-c.

Each spectrophotometer 117a, 117b and 117c is configured here to be connected on the supply line, upstream, to a respective pressure sensor 116a, 116b and 116c.

The installation 1 further comprises continuity valves 121a, 121b and 121c, reserve valves 122a, 122b and 122c, and outlet valves 123a, 123b and 123c, which are mounted on a support block 124 of cabinet form, disposed on the second part 106 of the third lower frame 103 of the third chassis 102. It will be noted that the continuity valves 121a, 121b and 121c and the reserve valves 122a, 122b and 122c may also be called outlet valves since they are located downstream of the columns.

The continuity valves 121a are mounted on an upper face of the support block 124 whereas the reserve valves 122a, 122b and 122c and outlet valves 123a, 123b and 123c are mounted on a lateral face of the support block 124 on the first free side 107 of the third cart 4.

These continuity 121a-c, reserve 122a-c and outlet 123a-c valves are all similar here to the distribution valves 81a-c, 82a-c and 83a-c, to the filter valves 62 and 65, to the supply valves 20a and 20b and to the inlet valves 18a to 18e.

In particular, the continuity 121a-c, reserve 122a-c and outlet 123a-c valves are each provided with a body housed in the support block 124 and with a head extending the body and which projects from the respective upper or lateral face of the support block 124.

What is more, these continuity 121a-c, reserve 122a-c and outlet 123a-c valves are multitube pinch valves like those described earlier.

The continuity valve 121a is configured here to be connected on the supply line, downstream, to the spectrophotometer 117a and, upstream, in particular to the distribution valve 82c connected to the column 99c so as to create a fluid loop from the column 99a to the column 99c.

The continuity valve 121b is configured here to be connected on the supply line, downstream, to the spectrophotometer 117b and, upstream, in particular to the distribution valve 82a connected to the column 99a so as to create a fluid loop from the column 99b to the column 99a.

The continuity valve 121c is configured here to be connected on the supply line, downstream, to the spectrophotometer 117c and, upstream, in particular to the distribution valve 82b connected to the column 99b so as to create a fluid loop from the column 99a to the column 99b.

Each of the reserve valves 122a, 122b and 122c is configured here to be connected, upstream, on the supply line to the respective continuity valve 121a, 121b and 121c and, downstream, in particular on a reserve line to the reserve container, itself configured to be connected to the supply valve 20a.

Each of the outlet valves 123a, 123b and 123c is configured here to be connected, on the supply line, upstream, to the respective reserve valve 122a, 122b and 122c and, downstream, to what is referred to as a fraction container and to a waste container, according to the state of the respective valve.

With reference to FIG. 2, the third cart 4 is moved towards the first cart 2 until it is juxtaposed against it, by a second side 125 of the third cart 4, which is an opposite side to its free first side 107, with the second side 13 of the first cart 2.

In this configuration, the first chassis 5 of the first cart 2 and the third chassis 102 of the third cart 4 are in abutment against each other, with the top of the third chassis 102, formed by the two longitudinal bars, being partially nested under the portion of the support plate 16 of the first cart 2 which projects from the first chassis 5.

It will be noted that the first and third carts 2 and 4 have the same depth, in the transverse direction, and that the arrangement of one relative to the other is made such that the receiving space 110 formed in the third chassis 102 remains accessible equally by the front 104 and by the top of the third cart 4, in particular via the cut-out 79 formed in the portion of the support plate 16 which projects from the first chassis 5.

With reference now to FIG. 3, the second cart 3, already prepared with the three columns 99a-c, is moved towards the assembly formed by the first and third carts 2 and 4 then inserted by the front 104 into the receiving space 110 formed in the third chassis 102 of the third cart 4.

In this configuration, the second chassis 95 of the second cart 3 is substantially sandwiched in the third lower frame 103 of the third chassis 102 of the third cart 4, and the columns 99*a-c* are disposed substantially beneath the control and actuation platforms 80*a-c* and the additional instrument supports 111*a-c* and are accessible from the top of the installation 1, and in particular from the cut-out 79 and part of the opening formed on the top of the third chassis 102, between the two transverse bars and the longitudinal bar which is located towards the first free side 107 of the third cart 4.

It will be noted that the second cart 3 has a depth which enables it not to go beyond the floor space occupied on the ground, in depth, taken by the first and third carts 2 and 4, except at the front 107 towards the front 107 of the third cart 4 where the maneuvering handle 99 remains accessible.

It will also be noted that in this configuration, a control and actuation platform 80*a-c* and an additional instrument support 111*a-c* are dedicated to a respective column 99*a-c*.

The arrangement of the first, second and third carts 2 to 4 and of the components which they comprise makes it possible to provide a particularly compact, flexible and intuitive topography of the treatment circuit and of these components that make it up.

In particular, it is particularly visible that the supply line and the additional line extend longitudinally, substantially in parallel, from the supply valves 20*a-b* and the inlet valves 18*a-e*, to the dedicated control and actuation platforms 80*a-c*.

It is also particularly visible that the supply line then continues along three branches of the treatment circuit which extend over a short longitudinal distance but which pass, substantially in parallel, from the dedicated control and actuation platforms 80*a-c* to the additional instrument supports 111*a-c*, passing via the columns 99*a-c*, and more generally to the outlet valves 123*a-c*.

This makes it possible in particular to give a shorter length for all the carts 2 to 4, while limiting their depth, on account of the triangular disposition of the three columns 99*a-c*, but also of the platforms 80*a-c* and also of the additional instrument supports 111*a-c*.

This also makes it possible to provide a treatment circuit with shorter lengths of pipes and substantially similar lengths, over the first part of the circuit from the supply valves 20*a-b* and the inlet valves 18*a-e* to the dedicated control and actuation platforms 80*a-c*, and/or over the second part of the circuit from the dedicated control and actuation platforms 80*a-c* to the columns 99*a-c*, and/or over the third part of the circuit from the columns 99*a-c* to the outlet valves 123*a-c*; so as to ensure continuity of treatment, as explained later.

A description will now be made of the treatment circuit and of a method of treatment by chromatography using the treatment circuit provided by the installation and illustrated diagrammatically in FIGS. 11 and 12.

In these drawings, references 200, 210 and 220 are respectively given to the supply line, the additional line and to the reserve line of the circuit.

It will be noted that the term "pipe" may be comprised in the present document as a portion of piping, preferably flexible and disposable, linking components of the circuit, it being possible for this portion equally well to comprise a single duct or on the contrary several ducts possibly having different diameters.

The biological liquid to treat is initially located in what is referred to as a source container or in a source bag 130 filled with liquid coming from a bioreactor or coming from a later treatment. This source bag 130 is connected via a connector to a first pipe 131 which is connected to the supply valve 20*b* on the supply line 200. The air presence sensor 22 is also connected on this first pipe 131, between the bag 130 and the valve 20*b*.

The biological liquid to treat may also be located in a reserve container 132 filled with liquid coming from a step of treatment by chromatography (see below). This reserve container 132 is connected via a connector to a second pipe 133 which is connected to the supply valve 20*a* on the supply line 200.

A first equilibration buffer product is initially located in a first equilibration container 134 which is connected via a connector to a main pipe 135 of the supply line 200, which main pipe 135 is connected to the supply valve 20*a* and passes from that first equilibration container 134 to a first branching connector 136, or distributor, of the installation 1 (see below), where that main pipe 135 subdivides into three branches 135*a*, 135*b* and 135*c*.

A second equilibration buffer product is initially located in a second equilibration container 137 which is connected via a connector to an additional pipe 143 of the additional line 210, which additional pipe 143 is connected to the inlet valve 18*a* and passes from that second equilibration container 137 to a second branching connector 149, or distributor, of the installation 1 (see below), where that additional pipe 143 subdivides into three branches 143*a*, 143*b* and 143*c*.

A first washing product is initially located in a first washing container 138 which is connected via a connector to a third pipe 144 which is connected to the inlet valve 18*a* on the additional line 210.

A second washing product is initially located in a second washing container 139 which is connected via a connector to a fourth pipe 145 which is connected to the inlet valve 18*b* on the additional line 210.

An elution product is initially located in an elution container 140 which is connected via a connector to a fifth pipe 146 which is connected to the inlet valve 18*c* on the additional line 210.

A cleaning product is initially located in a cleaning container 141 which is connected via a connector to a sixth pipe 147 which is connected to the inlet valve 18*d* on the additional line 210.

A regeneration product is initially located in a regeneration container 141 which is connected via a connector to a seventh pipe 148 which is connected to the inlet valve 18*e* on the additional line 210.

As indicated above, it is to be recalled that the two-way valve 21, the flowmeter 24, the supply pump 30, the pressure sensor with safety feature 33, the first drain valve 36, the first and second debubbler valves 38 and 40, the third drain valve 54, the first and second filter valves 62 and 65, and the fourth pressure sensor 70 are successively installed on the main pipe 135 of the supply line 200, from the supply valve 20*b* to the first branching connector 136.

The first drain valve 36 is connected here to an eighth pipe 150 to which is connected, via a connector, a waste container 151.

The first debubbler valve 38 is connected here to a ninth pipe 152 to which is connected, via a connector, the inlet of the first debubbler 48, and the second debubbler valve 40 is connected here to a tenth pipe 153 to which is connected, via a connector, the main outlet of the first debubbler 48.

The third drain valve 54 is connected here to an eleventh pipe 154 to which is connected, via a connector, a waste container 155.

The first filter valve 62 is connected here to a twelfth pipe 156 to which is connected, via a connector, the inlet of the filter 64, and the second filter valve 65 is connected here to a thirteenth pipe 157 to which is connected, via a connector, the outlet of the filter 64.

As indicated above, it is to be recalled that the two-way valve 19, the flowmeter 25, the additional pump 32, the pressure sensor with safety feature 35, the second drain valve 42, the third and fourth debubbler valves 44 and 46, the fourth drain valve 56, and the fifth pressure sensor 72 are successively installed on the additional pipe 143 of the additional line 210 from the inlet valve 18e to the second branching connector 149.

The second drain valve 42 is connected here to a fourteenth pipe 158 to which is connected, via a connector, a waste container 159.

The third debubbler valve 44 is connected here to a fifteenth pipe 160 to which is connected, via a connector, the inlet of the second debubbler 49, and the fourth debubbler valve 46 is connected here to a sixteenth pipe 161 to which is connected, via a connector, the main outlet of the second debubbler 49.

The fourth drain valve 56 is connected here to a seventeenth pipe 162 to which is connected, via a connector, a waste container 163.

What is more, the distribution valves 81a and 82a, the conductivity 78a, pH 85a and air presence 86a sensors, via the dedicated control and actuation platform 80a the distribution valve 83a the chromatography column 99a and a manual valve 190a associated with the column 99a at the outlet of the latter, the conductivity 113a, pH 114a and UV radiation 115a sensors, via the dedicated additional instrument support 111a, the pressure sensor 116a, the spectrophotometer 117a and the continuity 121a, reserve 122a and outlet 123a valves are successively installed on the branch 135a of the main pipe 135 on the supply line 200, from the first branching connector 136.

The distribution valve 81a is connected here, upstream, to the first branching connector 136 and, downstream, to the branch 143a of the additional pipe 143.

The distribution valve 82a is connected here, upstream, to the distribution valve 81a and, downstream, to a first continuity pipe 170 and to the instrument members of the platform 80a.

The distribution valve 83a is connected here, downstream, to the instrument members of the platform 80a and, upstream, to an eighteenth pipe 163 to which is connected, via a connector, a waste container 164, and to the instrument members of the additional support 111a.

The continuity valve 121a is connected here, upstream, to the spectrophotometer 117a and, downstream, to a second continuity pipe 171 and to the reserve valve 122a.

The reserve valve 122a is connected here, upstream, to the continuity valve 121a and, downstream, to a reserve pipe 165 and to the outlet valve 123a. This reserve pipe 165 is connected here, via a connector, to the reserve container 132.

The outlet valve 123a is connected here, upstream, to the reserve valve 122a and, downstream, to a nineteenth pipe 166 to which is connected, via a connector, a fraction container 167, and to a waste container 168 via another connector connected to the branch 135a of the main pipe 135.

The distribution valves 81b and 82b, the conductivity 78b, pH 85b and air presence 86b sensors, via the dedicated control and actuation platform 80b, the distribution valve 83b, the chromatography column 99b and a manual valve 190b associated with the column 99b at the outlet of the latter, the conductivity 113b, pH 114b and UV radiation 115b sensors, via the dedicated additional instrument support 111b, the pressure sensor 116b, the spectrophotometer 117b, and the continuity 121b, reserve 122b and outlet 123b valves are successively installed on the arm 135b of the main pipe 135 on the supply line 200, from the first branching connector 136.

The distribution valve 81b is connected here, upstream, to the first branching connector 136 and, downstream, to the branch 143b of the additional pipe 143.

The distribution valve 82b is connected here, upstream, to the distribution valve 81b and, downstream, to a third continuity pipe 172 and to the instrument members of the platform 80b.

The distribution valve 83b is connected here, downstream, to the instrument members of the platform 80b and, upstream, to a twenty-first pipe 173 to which is connected, via a connector, a waste container 175, and to the instrument members of the additional support 111b.

The continuity valve 121b is connected here, upstream, to the spectrophotometer 117b and, downstream, to the first continuity pipe 170 and to the reserve valve 122b.

The reserve valve 122b is connected here, upstream, to the continuity valve 121b and, downstream, to a first annex reserve pipe 175 and to the outlet valve 123b. This first annex reserve pipe 175 is linked to the reserve pipe 165.

The outlet valve 123b is connected here, upstream, to the reserve valve 122b and, downstream, to a first annex fraction pipe 176 which is linked to the fraction pipe 166, and to a waste container 177 via a connector connected on the branch 135b of the main pipe 135.

What is more, the distribution valves 81c and 82c the conductivity 78c, pH 85c and air presence 86c sensors, via the dedicated control and actuation plafform 80c, the distribution valve 83c, the chromatography column 99c and a manual valve 190c associated with the column 99c at the outlet of the latter, the conductivity 113c, pH 114c and UV radiation 115c sensors, via the dedicated additional instrument support 111c, the pressure sensor 116c, the spectrophotometer 117c, and the continuity 121c, reserve 122c and outlet 123c valves are successively installed on the arm 135c of the main pipe 135 on the supply line 200, from the first branching connector 136.

The distribution valve 81c is connected here, upstream, to the first branching connector 136 and, downstream, to the branch 143c of the additional pipe 143.

The distribution valve 82c is connected here, upstream, to the distribution valve 81c and, downstream, to a second continuity pipe 171 and to the instrument members of the platform 80c.

The distribution valve 83c is connected here, downstream, to the instrument members of the platform 80c and, upstream, to an twenty-second pipe 178 to which is connected, via a connector, a waste container 179, and to the instrument members of the additional support 111c.

The continuity valve 121c is connected here, upstream, to the spectrophotometer 117c and, downstream, to the third continuity pipe 172 and to the reserve valve 122c.

The reserve valve 122c is connected here, upstream, to the continuity valve 121c and, downstream, to a second annex reserve pipe 180 and to the outlet valve 123c. This second annex reserve pipe 180 is linked to the reserve pipe 165 via the first annex reserve pipe 175.

The outlet valve 123c is connected here, upstream, to the reserve valve 122c and, downstream, to a second annex fraction pipe 181 which is linked to the fraction pipe 166 via the first annex fraction pipe 176, and to a waste container 182 via a connector connected to the branch 135c of the main pipe 135.

The treatment by chromatography using the circuit described above may comprise the following steps.

A step of preparing the circuit is implemented, with a first filling phase.

For this, the first and second equilibration containers 134 and 137 are connected to the main and additional pipes 135 and 143. The valves 18a-e, 19, 20a-b, 21, 36, 38, 40, 42, 44, 46, 54, 56, 62, 65, 81a-c, 82a-c and 83a-c, the pumps 30 and 32, and the branching connectors 136 and 149 are controlled to make the equilibration liquid flow in parallel in the main 135 and additional 143 pipes, passing via the first and second debubblers 48 and 49 and by the filter 64 but shunting the waste containers 151, 155, 159 and 163, to reach the valves 83a-c which direct the liquid into the waste containers 164, 174 and 179, ahead of the columns 99a-c.

A second filling phase is implemented. For this, only the second equilibration container 137 is connected. The valves 18a-e, 19, 42, 44, 46, 81c, 82a-c, 83a-c and 121a-c, the additional pump 32, and the second branching connector 149 are controlled to make the equilibration liquid flow, successively, in the additional pipe 143, shunting the second debubbler 49 and the waste containers 159 and 163, in the branch 135c of the main pipe 135, through the column 99c (shunting the waste container 179) and in the third continuity pipe 172 to reach the valve 83b which directs the liquid into the waste container 174 ahead of the column 99b.

When the air presence sensor 86c no longer detects air, the valve 83b is controlled to shunt the waste container 174 and in order for the liquid to be conveyed beyond the preceding path, through the column 99b and into the first continuity pipe 170 to reach the valve 83a which directs the liquid into the waste container 164 ahead of the column 99a.

When the air presence sensor 86a no longer detects air, the valve 83a is controlled to shunt the waste container 164 and in order for the liquid to be conveyed beyond the previous path, through the column 99a and into the second continuity pipe 171.

It will be noted that the two filling phases may be implemented with a product other than the equilibration buffer product.

An equilibration phase successively to each of the columns 99a-c is next implemented.

For this, only the second equilibration container 137 is connected. The valves 18a-e, 19, 42, 44, 46, 81c, 82c, 83c, 121c, 122c and 123c, the additional pump 32, and the second branching connector 149 are controlled to make the equilibration liquid pass in the additional pipe 143, shunting the second debubbler 49 and the waste containers 159 and 163, in the branch 135c of the main pipe 135, through the column 99c (shunting the waste container 179) to reach the valve 123c which directs the liquid into the waste container 182; until the values of pH and conductivity measured by the sensors 113c and 114c after the column 99c are identical to the values of pH and conductivity measured by the sensors 78c and 85c, ahead of the column 99c.

Next, the second equilibration container 137 is connected, the valves 18a-e, 19, 42, 44, 46, 81b, 82b, 83b, 121b, 122b and 123b, the additional pump 32, and the second branching connector 149 are controlled to make the equilibration liquid pass in the additional pipe 143, shunting the second debubbler 49 and the waste containers 159 and 163, in the branch 135b of the main pipe 135, through the column 99b (shunting the waste container 174) to reach the valve 123b which directs the liquid into the waste container 177; until the values of pH and of conductivity measured by the sensors 113b and 114b after the column 99b are identical of the values of pH and of conductivity measured by the sensors 78b and 85b, ahead of the column 99b.

Next, the second equilibration container 137 is connected, the valves 18a-e, 19, 42, 44, 46, 81a, 82a, 83a, 121a, 122a and 123a, the additional pump 32, and the second branching connector 149 are controlled to make the equilibration liquid pass in the additional pipe 143, shunting the second debubbler 49 and the waste containers 159 and 163, in the branch 135a of the main pipe 135, through the column 99a (shunting the waste container 164) to reach the valve 123a which directs the liquid into the waste container 168; until the values of pH and of conductivity measured by the sensors 113a and 114a after the column 99a are identical of the values of pH and of conductivity measured by the sensors 78a and 85a, ahead of the column 99a.

A first loading phase can be carried out. For this, the product container 130 (or flexible bag) is connected to the first pipe 131. The valves 20b, 21, 36, 38, 40, 54, 62, 65, 81c, 82c, 83c, 121c, 82b, 83b, 121b, 122b and 123b, the first branching connector 136 and the supply pump 30 are controlled to cause to flow the biological liquid to treat, successively, in the main pipe 135 passing via the first debubbler 48, by the filter 64, shunting the waste containers 151 and 155, then in the branch 135c shunting the waste container 179 and passing through the column 99c, then into the third continuity pipe 172, then into the branch 135b, shunting the waste container 174, passing through the column 99b, shunting the reserve 132 and fraction 167 containers, to reach the valve 123b which directs the treated liquid into the waste container 177.

A new loading phase may be carried out, in particular when the column 99c is what is referred to as loaded. For this, the product container 130 (or flexible bag) is still connected to the first pipe 131. The valves 20b, 21, 36, 38, 40, 54, 62, 65, 81b, 82b, 83b, 121b, 82a, 83a, 121a, 122a and 123a, the first branching connector 136 and the supply pump 30 are controlled to cause to flow the biological liquid to treat, successively, in the main pipe 135 passing via the first debubbler 48, by the filter 64, shunting the waste containers 151 and 155, then in the branch 135b shunting the waste container 174 and passing through the column 99c then into the first continuity pipe 170, then into the branch 135a, shunting the waste container 164, passing through the column 99a, shunting the reserve 132 and fraction 167 containers, to reach the valve 123a which directs the treated liquid into the waste container 168.

In parallel with this new loading phase, a phase of recovery and preparation of the column 99c may be carried out. For this, the first and second washing containers 138 and 139, the elution container 140, the cleaning container 141 and the regeneration container 142 are connected to the respective pipes 144 to 148. The valves 18a-e, 19, 42, 44, 46, 56, 81c, 82c, 83c, 121c, 122c and 123c, the second branching connector 149 and the additional pump 32 are controlled to make flow:

the first cleaning liquid in the additional pipe 143, passing via the second debubbler 49 and shunting the waste containers 159 and 163, then in the branch 135c, shunting the waste container 179, passing through the column 99c, either to reach the reserve valve 122c which directs the first cleaning liquid to the reserve container 132 for retreatment, or to reach the outlet valve 123c (shunting the fraction container 167) which directs the first cleaning liquid to the waste container 182; then optionally, the second cleaning liquid in the additional pipe 143, passing via the second debubbler 49 and shunting the waste containers 159 and 163, then in the branch 135c, shunting the waste container 179, passing through the column 99c, to reach the outlet valve 123c (shunting the reserve container 132 and the fraction container 167) which directs the second cleaning liquid to the waste container 182; then the elution liquid in the additional pipe 143, passing via the second debubbler 49 and shunting the waste containers 159 and 163, then in the branch 135c, shunting the waste container 179, passing through the column 99c, to reach the outlet valve 123c which directs the elution liquid to the fraction container 167, shunting the reserve container 132, when the elution peak is detected using the UV sensor 115c; then the cleaning liquid in the additional pipe 143, passing via the second debubbler 49 and shunting the waste containers 159 and 163, then in the branch 135c, shunting the waste container 179, passing through the column 99c, to reach the outlet valve 123c which directs the cleaning liquid to the waste container 182 (shunting the reserve container 132 and the fraction container 167); then the regeneration liquid in the additional pipe 143, passing via the second debubbler 49 and shunting the waste containers 159 and 163, then in the branch 135c, shunting the waste container 179, passing through the column 99c, to reach the outlet valve 123c which directs the regeneration liquid to the waste container 182 (shunting the reserve container 132 and the fraction container 167).

A new loading phase may be carried out, in particular when the column 99b is said to be loaded. For this, the product container 130 (or flexible bag) is still connected to the first pipe 131. The valves 20b, 21, 36, 38, 40, 54, 62, 65, 81a, 82a, 83a, 121a, 82c, 83c, 121c, 122c and 123c, the first branching connector 136 and the supply pump 30 are controlled to cause to flow the biological liquid to treat, successively, in the main pipe 135 passing via the first debubbler 48, by the filter 64, shunting the waste containers 151 and 155, then in the branch 135a, shunting the waste container 164 and passing through the column 99a, then into the second continuity pipe 171, then into the branch 135c, shunting the waste container 179, passing through the column 99c, shunting the reserve 132 and fraction 167 containers, to reach the valve 123c which directs the treated liquid into the waste container 182.

In parallel with this new loading phase, a phase of recovery and preparation of the column 99b may be carried out. For this, the first and second washing containers 138 and 139, the elution container 140, the cleaning container 141 and the regeneration container 142 are connected to the respective pipes 144 to 148. The valves 18a-e, 19, 42, 44, 46, 56, 81b, 82b, 83b, 121b, 122b and 123b, the second branching connector 149 and the additional pump 32 are controlled to make flow:

the first cleaning liquid in the additional pipe 143, passing via the second debubbler 49 and shunting the waste containers 159 and 163, then in the branch 135b, shunting the waste container 174, passing through the column 99b, either to reach the reserve valve 122b which directs the first cleaning liquid to the reserve container 132 for retreatment, or to reach the outlet valve 123b (shunting the fraction container 167) which directs the first cleaning liquid to the waste container 177; then optionally, the second cleaning liquid in the additional pipe 143, passing via the second debubbler 49 and shunting the waste containers 159 and 163, then in the branch 135b, shunting the waste container 174, passing through the column 99b, to reach the outlet valve 123b (shunting the reserve container 132 and the fraction container 167) which directs the second cleaning liquid to the waste container 177; then the elution liquid in the additional pipe 143, passing via the second debubbler 49 and shunting the waste containers 159 and 163, then in the branch 135b, shunting the waste container 174, passing through the column 99b, to reach the outlet valve 123b which directs the elution liquid to the fraction container 167, shunting the reserve container 132, when the elution peak is detected using the UV sensor 115b; then the cleaning liquid in the additional pipe 143, passing via the second debubbler 49 and shunting the waste containers 159 and 163, then in the branch 135b, shunting the waste container 174, passing through the column 99b, to reach the outlet valve 123b which directs the cleaning liquid to the waste container 177 (shunting the reserve container 132 and the fraction container 167); then the regeneration liquid in the additional pipe 143, passing via the second debubbler 49 and shunting the waste containers 159 and 163, then in the branch 135b, shunting the waste container 174, passing through the column 99b, to reach the outlet valve 123b which directs the regeneration liquid to the waste container 177 (shunting the reserve container 132 and the fraction container 167).

A new loading phase may be carried out, in particular when the column 99a is said to be loaded. This new loading phase is identical to the previous phase referred to as first loading, with the biological liquid passing through the columns 99c then 99b. Alternatively, this new loading phase may be carried out by virtue of the connection of the reserve container 132 to the supply valve 20a rather than the connection of the product container 130, so as to treat the recovered first cleaning product.

In parallel with this new loading phase, a phase of recovery and preparation of the column 99a may be carried out. For this, the first and second washing containers 138 and 139, the elution container 140, the cleaning container 141 and the regeneration container 142 are connected to the respective pipes 144 to 148. The valves 18a-e, 19, 42, 44, 46, 56, 81a, 82a, 83a, 121a, 122a and 123a, the second branching connector 149 and the additional pump 32 are controlled to make flow:

the first cleaning liquid in the additional pipe 143, passing via the second debubbler 49 and shunting the waste containers 159 and 163, then in the branch 135a, shunting the waste container 164, passing through the column 99a, either to reach the reserve valve 122a which directs the first cleaning liquid to the reserve container 132 for retreatment, or to reach the outlet valve 123a (shunting the fraction container 167) which directs the first cleaning liquid to the waste container 168; then optionally, the second cleaning liquid in the additional pipe 143, passing via the second debubbler 49 and shunting the waste containers 159 and 163, then in the branch 135a, shunting the waste container 164, passing through the column 99a, to reach the outlet valve 123a (shunting the reserve container 132 and the fraction container 167) which directs the second cleaning liquid to the waste container 168; then the elution liquid in the additional pipe 143, passing via the second debubbler 49 and shunting the waste containers 159 and 163, then in the branch 135a, shunting the waste container 164, passing through the column 99a, to reach the outlet valve 123a which directs the elution liquid to the fraction container 167, shunting the reserve container 132, when the elution peak is detected using the UV sensor 115a; then the cleaning liquid in the additional pipe 143, passing via the second debubbler 49 and shunting the waste containers 159 and 163, then in the branch 135a, shunting the waste container 164, passing through the column 99a, to reach the outlet valve 123a which directs the cleaning liquid to the waste container 168 (shunting the reserve container 132 and the fraction container 167); then the regeneration liquid in the additional pipe 143, passing via the second debubbler 49 and shunting the waste containers 159 and 163, then in the branch 135a, shunting the waste container 164, passing through the column 99a, to reach the outlet valve 123a which directs the regeneration liquid to the waste container 168 (shunting the reserve container 132 and the fraction container 167).

The treatment can proceed continuously, employing again the same phases as those described above.

Of course, here, the treatment began with the placing in series of the columns 99c and 99b but it could begin with the placing in series of for example the columns 99b and 99a or 99a and 99c.

Furthermore, it is to be noted that the manual valves 190a-c are by default open during the whole of the chromatography treatment, provided that the columns 99a-c are connected on the circuit. They are closed when the treatment is terminated and the columns 99a-c are removed from the circuit of the installation.

In variants that are not illustrated:
the installation may comprise more than three chromatography columns, or even only two chromatography columns;
the columns could be disposed in a circle or diamond rather than in a triangle;
the installation may comprise more or fewer control and actuation platforms, or even additional instrument supports, according to the number of chromatography columns;
the installation may comprise more or fewer instrument members mounted on each control and actuation platform;
the installation may lack any spectrophotometer, or only comprise a single spectrophotometer, situated as on the shelf of the third cart or situated on an annex support, not accommodated on the third cart, and configured to be connected to the nineteenth pipe 166 just before the fraction container 167;
the additional instrument supports and the instrument members they comprise could also be mounted, for example in the vertical orientation, on the control and actuation platforms, while maintaining their so-called post-column instrument functions; such that the control and actuation platforms would at the same time provide what are referred to as pre-column and post-column instrument functions;
the installation could be provided with only two carts, the first and second carts being combined, or the first and third carts being combined or the second and third carts being combined, or even only one cart, or on the contrary more than three carts;
the arrangement of the instrument members upstream and downstream of the vertical platforms could be different on the main cabinet, on the support plate and on the third chassis; and
the phases implemented in the treatment by chromatography could be different from that described above, in particular for the purpose of the recovery and preparation of the loaded column.

It should be noted more generally that the invention is not limited to the examples described and represented.

The invention claimed is:

1. An installation for treating biological liquid by chromatography, generally extending in a longitudinal direction and comprising:
at least one supply valve (20b) for supplying biological liquid to treat, configured to be connected to at least one biological liquid supply container (130);
at least one supply pump (30) disposed downstream of said at least one supply valve and connected to the latter;
a plurality of instrument members disposed downstream of said at least one supply pump, including at least one distribution valve (81a-c, 82a-c, 83a-c) and at least one device (78a-c, 85a-c, 86a-c) for measuring a physicochemical parameter of the biological liquid, and which are connected to said at least one supply pump;
at least one chromatography column (99a-c) disposed downstream of said plurality of instrument members and directly associated with and connected to at least some of them, and configured to be supplied with biological liquid by said at least one supply pump; and
a plurality of single-use pipes configured to be connected to said at least one supply valve, to said at least one supply pump, to said plurality of instrument members and to said at least one chromatography column, so as to form at least one supply line (200) for supplying biological liquid to treat of a treatment circuit of said installation;
characterized in that said instrument members associated with said at least one chromatography column are each mounted on at least one dedicated control and actuation platform (80a-c), which extends in a vertical direction relative to the longitudinal direction of extension of said installation, and are disposed above each other on said dedicated control and actuation platform; and
characterized in that said distribution valves (81a-c, 82a-c, 83a-c) are each provided with a valve body and a valve head which extends from said body and which is provided to receive at least portions of pipes of said supply line, and said at least one control and actuation platform (80a-c) comprises a support block (84a-c) which extends vertically, in which are housed said valve bodies and from which said valve heads project laterally, as well as a support plate (89a-c) fastened to said support block and having an arm (191a-c) which projects from said support block and on which is mounted said at least one measuring device (78a-c, 85a-c, 86a-c).

2. An installation according to claim 1, characterized in that said at least one control and actuation platform (80a-c) comprises several distribution valves (81a-c, 82a-c, 83a-c) and one or more measuring devices chosen from a conductivity sensor (78a-c) and/or a pH sensor (85a-c) and/or an air presence sensor (86a-c).

3. An installation according to claim 1, characterized in that the installation comprises several chromatography columns (99a-c) disposed downstream of said at least one control and actuation platform (80a-c), and which extend in a direction generally transverse to said generally longitudinal direction of extension of said installation.

4. An installation according to claim 3, characterized in that the installation comprises several dedicated control and actuation platforms (80a-c), each being individually associated with one of said chromatography columns (99a-c), said dedicated control and actuation platforms being disposed in the same generally transverse direction as said chromatography columns.

5. An installation according to claim 4, characterized in that said control and actuation platforms (80a-c) are mounted on a first cart (2) and said chromatography columns (99a-c) are mounted on a second cart (3) configured to be juxtaposed against and/or partially nested with said first cart.

6. An installation according to claim 5, characterized in that said first cart (2) comprises a first chassis (5), at least one electrical and pneumatic distribution cabinet (14) mounted on said chassis and on which is disposed said at least one supply valve (20b), at least one receiving space (59) formed in said first chassis and provided to receive containers for recovery of liquids, and at least one support plate (16) mounted in a projecting manner on said first chassis and on which are disposed said at least one supply pump (30) and said control and actuation platforms (80a-c), and said second cart (3) comprises a second chassis (95) provided with a support board provided to receive said chromatography columns (99a-c) and configured to come at least partially to nest under said support plate (16) of said first cart.

7. An Installation according to claim 6, characterized in that said additional instrument supports (111a-c) are mounted on a third cart (4) configured to be juxtaposed against and/or partially nested with said first cart (2) and/or with said second cart (3).

8. An installation according to claim 7, characterized in that the installation further comprises a plurality of supplementary instrument members disposed downstream of said chromatography columns (99a-c), including at least one outlet valve (121a-c, 122a-c, 123a-c) and at least one supplementary measuring device chosen from a pressure sensor (116a-c) and/or a spectrophotometer (117a-c), said supplementary instrument members being mounted on said third cart (4), downstream of said additional instrument supports (111a-c).

9. An installation according to claim 8, characterized in that said third cart (4) comprises a third chassis (102), substantially the shape of an inverted U, on which are mounted at least said additional instrument supports (111a-c) at a free end of said third chassis, and which is configured to be juxtaposed against said first chassis (5) of said first cart (2) by an opposite end to its free end, and to nestingly receive, in a space (110) formed by the inverted U between its opposite end and its free end, said second chassis (95) of said second cart (3) provided with said chromatography columns (99a-c).

10. An installation according to claim 7, characterized in that said third cart (4) comprises a third chassis (102), substantially the shape of an inverted U, on which are mounted at least said additional instrument supports (111a-c) at a free end of said third chassis, and which is configured to be juxtaposed against said first chassis (5) of said first cart (2) by an opposite end to its free end, and to nestingly receive, in a space (110) formed by the inverted U between its opposite end and its free end, said second chassis (95) of said second cart (3) provided with said chromatography columns (99a-c).

11. An installation according to claim 1, characterized in that the installation further comprises additional instrument supports (11a-c) disposed downstream of said chromatography columns (99a-c) and on which are mounted one or more additional measuring devices chosen from a conductivity sensor (113a-c), and/or a pH sensor (114a-c) and/or a UV radiation sensor (115a-c).

12. An installation according to claim 11, characterized in that said additional instrument supports (111a-c) are mounted on a third cart (4) configured to be juxtaposed against and/or partially nested with said first cart (2) and/or with said second cart (3).

13. An installation according to claim 1, characterized in that said at least one supply valve and/or said at least one distribution valve are three-way valves, of which two ways are inlets and one an outlet or one an inlet and two outlets, and optionally, a valve provided with a head having two reception channels (91, 92) for portions of said pipes, and a pinching mechanism configured to allow or prevent the passage of said biological liquid in said portions of said pipes received in the two said channels (91, 92).

14. An installation according to claim 1, characterized in that the installation further comprises a reserve container (132) disposed downstream of said at least one chromatography column (99a-c) and connected to the latter, said reserve container being provided to receive a buffer product used for the cleaning of said at least one chromatography column after treatment of said biological liquid, and another supply valve (20a) disposed downstream of said reserve container and upstream of said at least one supply pump (30) and connected to the latter, said other supply valve (20a) being configured to re-introduce, via said at least one supply pump, said buffer product into said supply line (200) as liquid to treat in said at least one chromatography column (99a-c).

15. An installation according to claim 1, characterized in that the installation further comprises a plurality of inlet valves (18a-e) configured to be connected to containers (138-142) for what are referred to as buffer products and to supply said treatment circuit for the purpose of preparing and/or cleaning and/or elution and/or regeneration of said at least one chromatography column (99a-c), and at least one additional pump (32) disposed downstream of said inlet valves and upstream of said at least one chromatography column and connected to these latter; pipes of said plurality of single-use pipes being configured to be connected to said inlet valves and to said additional pump, so as to form at least one additional line (210), which extends substantially longitudinally and in parallel to said supply line (200), from respectively said inlet valves (18a-e) and said at least one supply valve (20b), to said at least one dedicated control and actuation platform (80a-c).

16. An installation according to claim 15, characterized in that the installation further comprises other instrument members, among which are, on said supply line (200):
  a product presence sensor (22) disposed upstream of said at least one supply valve (20b); and/or
  a two-way isolating valve (21) and/or a flow meter (24) disposed between said at least one supply valve and said at least one supply pump (30); and/or
  a pressure sensor (33) with or without a safety feature, and/or at least one drain valve (36, 54), and/or at least two debubbler valves (38, 40) and a debubbler (48) connected to each of these debubbler valves and/or at least one filter valve (62, 65) and a filter (64) connected to said at least one filter valve, which are disposed between said at least one supply pump and said at least one control and actuation platform (80*a-c*); and/or on said additional line (210):

a two-way isolating valve (19) and/or a flow meter (25) disposed between said inlet valves (18*a-e*) and said at least one additional pump (32); and/or at least one pressure sensor (35, 72) with or without a safety feature, and/or at least one drain valve (42, 56), and/or at least two debubbler valves (44, 46) and a debubbler (49) connected to each of those debubbler valves, disposed between said additional pump and said at least one control and actuation platform.

* * * * *